United States Patent
Brandt et al.

(10) Patent No.: US 11,733,029 B2
(45) Date of Patent: Aug. 22, 2023

(54) METHOD FOR ESTIMATING SHAPE PARAMETERS OF THE FOVEA BY OPTICAL COHERENCE TOMOGRAPHY

(71) Applicant: CHARITÉ UNIVERSITÄTSMEDIZIN BERLIN, Berlin (DE)

(72) Inventors: Alexander Brandt, Wesel (DE); Ella Maria Kadas, Berlin (DE); Sunil Yumar Yadav, Berlin (DE); Seyedamirhosein Motamedi, Berlin (DE); Paul Friedemann, Berlin (DE)

(73) Assignee: CHARITÉ UNIVERSITÄTSMEDIZIN BERLIN, Berlin (DE)

( * ) Notice: Subject to any disclaimer, the term of this patent is extended or adjusted under 35 U.S.C. 154(b) by 489 days.

(21) Appl. No.: 16/632,340

(22) PCT Filed: Jul. 19, 2018

(86) PCT No.: PCT/EP2018/069640
§ 371 (c)(1),
(2) Date: Jan. 18, 2020

(87) PCT Pub. No.: WO2019/016319
PCT Pub. Date: Jan. 24, 2019

(65) Prior Publication Data
US 2020/0170503 A1 Jun. 4, 2020

(30) Foreign Application Priority Data

Jul. 19, 2017 (EP) .................................... 17182192

(51) Int. Cl.
*G01B 9/02091* (2022.01)
*A61B 3/10* (2006.01)
*G06T 7/00* (2017.01)

(52) U.S. Cl.
CPC .......... *G01B 9/02091* (2013.01); *A61B 3/102* (2013.01); *G06T 7/0012* (2013.01);
(Continued)

(58) Field of Classification Search
CPC .. A61B 3/102; G01B 9/02091; G06T 7/0012; G06T 2207/10101; G06T 2207/30041
See application file for complete search history.

(56) References Cited

U.S. PATENT DOCUMENTS

2011/0181836 A1* 7/2011 Rowe ..................... G09B 23/34
351/205
2014/0122029 A1* 5/2014 Bodis-Wollner ........ G06F 30/20
703/1
(Continued)

FOREIGN PATENT DOCUMENTS

WO 2011048748 4/2011
WO WO-2017087018 A1 * 5/2017 ............. A61B 3/102

OTHER PUBLICATIONS

Scheibe et al "Parametric model for the 3D reconstruction of individual fovea shape from OCT data", Experimental Eye Research vol. 119, Feb. 2014, pp. 19-26, https://doi.org/10.1016/j.exer.2013.11.008.
(Continued)

*Primary Examiner* — Michael P LaPage
(74) *Attorney, Agent, or Firm* — JMB Davis Ben-David

(57) ABSTRACT

The invention relates to a method and a computer program for estimating shape parameters of an image data set (1) of a fovea (100), comprising the steps of:
  Acquiring an image data set (1) of a macula (50), comprising a foveal pit (101) and a foveal rim (102) at least partially,
  Estimating the center of the foveal pit (101) from the image data set (1),
(Continued)

Estimating from the center of the foveal pit (101), radially extending height profiles (c) of the fovea (100), For each height profile (c), fitting a model-function to the height profile (c), Estimating for each height profile (c) a set of fit parameters from the fitted model-function, Determining from the sets of estimated fit parameters at least one shape parameter of the fovea (100), particularly of the foveal pit (101).

Determining at least one shape feature of at least a part of the fovea.

11 Claims, 30 Drawing Sheets

(52) U.S. Cl.
CPC ............... *G06T 2207/10101* (2013.01); *G06T 2207/30041* (2013.01)

(56) References Cited

U.S. PATENT DOCUMENTS

| | | |
|---|---|---|
| 2016/0242638 A1 | 8/2016 | Durbin et al. |
| 2019/0279358 A1* | 9/2019 | Schaal ................... A61B 3/102 |
| 2020/0258295 A1* | 8/2020 | Hirokawa ............... G06T 17/00 |

OTHER PUBLICATIONS

Schiebe et al "Analysis of foveal characteristics and their asymmetries in the normal population", Exp Eye Res. Jul. 2016;148:1-11. doi: 10.1016/j.exer.2016.05.013. Epub May 15, 2016.

Ding et al "Application of an OCT data-based mathematical model of the foveal pit in Parkinson disease", J Neural Transm (Vienna). Nov. 2014;121(11):1367-76. doi: 10.1007/s00702-014-1214-2. Epub Apr. 20, 2014.

Liu et al "a sloped piecemeal gaussian model for characterising foveal pit shape", Ophthalmic Physiol Opt. Nov. 2016;36(6):615-631. doi: 10.1111/opo.12321.

\* cited by examiner

|  |  | HC | MS_NON | MS_ON | NMO_AQP4ab+_NON | NMO_AQP4ab+_ON | NMO_MOGab+_NON | NMO_MOGab+_ON | NMO_ab-_ON |
|---|---|---|---|---|---|---|---|---|---|
| Pit_Volume_mm3 | Mean | 0.24500223 | 0.25065309 | 0.23079463 | 0.271943125 | 0.24688245 | 0.241834667 | 0.231997923 | 0.207846 |
| Pit_Volume_mm3 | STD | 0.05236805 | 0.06307654 | 0.06417314 | 0.062171035 | 0.046043912 | 0.068841156 | 0.05250848 | 0.042898143 |
| Pit_Volume_mm3 | Max | 0.366672 | 0.450674 | 0.417068 | 0.384547 | 0.323516 | 0.34656 | 0.335289 | 0.243951 |
| Pit_Volume_mm3 | Min | 0.153285 | 0.134462 | 0.136484 | 0.153053 | 0.17071 | 0.168043 | 0.149284 | 0.139575 |

|  | HC | MS_NON | MS_ON | NMO_AQP4ab+_NON | NMO_AQP4ab+_ON | NMO_MOGab+_NON | NMO_MOGab+_ON | NMO_ab-_ON |
|---|---|---|---|---|---|---|---|---|
| Pit_Slope_deg Mean | 12.6718747 | 11.877381 | 11.1582323 | 10.69583522 | 9.084469 | 12.61879133 | 8.877439077 | 9.0084926 |
| Pit_Slope_deg STD | 2.4963705 | 2.63984578 | 1.57712146 | 2.823445982 | 3.333114746 | 3.217723648 | 2.656928863 | 1.712523424 |
| Pit_Slope_deg Max | 20.78964 | 17.339946 | 14.783368 | 16.231794 | 14.110915 | 16.168995 | 15.171015 | 11.720831 |
| Pit_Slope_deg Min | 6.806793 | 5.369515 | 8.454213 | 5.58219 | 3.408566 | 9.519343 | 6.081353 | 7.450734 |

Fig. 32

Table 5

|  | NMO | Rest |
|---|---|---|
| NMO | 37 | 15 |
| Rest | 10 | 168 |

True class (y-axis) / Predicted class (x-axis)

Fig. 33

Table 6

|  | NMO | Rest |
|---|---|---|
| NMO | 42 | 10 |
| Rest | 8 | 48 |

True class (y-axis) / Predicted class (x-axis)

Fig. 34

Table 7

|  | NMO | Rest |
|---|---|---|
| NMO | 35 | 17 |
| Rest | 11 | 111 |

True class (y-axis) / Predicted class (x-axis)

METHOD FOR ESTIMATING SHAPE PARAMETERS OF THE FOVEA BY OPTICAL COHERENCE TOMOGRAPHY

CROSS-REFERENCE TO RELATED APPLICATIONS

This is the U.S. National Stage of International Patent Application No. PCT/EP2018/069640 filed on Jul. 19, 2018, which in turn claims the benefit of European Patent Application No. 17182192.9 filed on Jul. 19, 2017.

Specification

The invention relates to a method and a computer program for estimating shape parameters of three-dimensional volume data of the fovea, particularly acquired with optical coherence tomography.

Optical coherence tomography (OCT) is a noninvasive method for imaging the human eye and for assessing pathological changes of the fovea and macula in many diseases.

OCT provides micrometer resolution in 3D retinal imaging, while providing comparably short measurement times.

Furthermore, it is known that multiple sclerosis (MS), neuromyelitis optica (also referred to as neuromyelitis optica spectrum disorders (NMO or NMOSD respectively)) as well as MOG-ab associated encephalomyelitis (MOG) are autoimmune neuroinflammatory diseases that exhibit similar phenotypes, but differ pathophysiologically. These diseases all occur with optic neuritis (ON), which is known to affect the retina.

While diagnosis of these diseases is done in a variety of ways and often established by using several diagnosing techniques, such as magnet-resonance imaging (MRI) or antibody tests, it is also known that many of these diseases can also be detected evaluating OCT data sets of the retina and specifically the fovea.

However, it is difficult to distinguish these neuroinflammatory diseases from each other on basis of OCT data sets and to detect differences in retinal damage other than caused by ON.

Despite there being a variety of approaches in OCT to study and quantify the morphological features of the fovea, none of these approaches has been used for differential diagnosis of MS, NMO, MOG or ON.

Differential diagnosis for the above mentioned diseases or disorders is complicated with conventional techniques and might take several days and sometimes up to years to be established, as for example only 30%-60% of NMO or MOG positive patients are tested positive by an dedicated antibody test.

On the other hand, it has not been established, whether the shape alteration of the fovea caused by these diseases is specific enough or at all specific to allow a distinction between NMO, MOG, MS and ON in the first place. A differential diagnosis by visual inspection is not possible.

Assuming the above-mentioned diseases exhibit specific shape alterations of the fovea, conventional OCT-based methods so far have not proven sensitive enough to reliably extract shape parameters describing the morphological structure of the fovea.

One approach to estimate relevant shape parameters of the fovea is taught by Dubis et al [2]. The authors modelled the fovea with a model-function for the foveal pit consisting of a Difference of Gaussian (DoG) function. However the DoG function exhibits a symmetrical shape, while the morphology of the fovea is not. Therefore, this approach cannot be sensitive enough for establishing a diagnosis due to the unsuitable model-function.

Scheibe et al. discloses a different approach to overcome these drawbacks by creating a more flexible 2D model, which is fitted to each supporting direction in a circular region around the foveal center [9]. This method uses a Gaussian like model-function $\exp(-x^a)$, with a being a fit parameter. The model-function is capable of accounting for the asymmetric shape of the fovea.

Although capable of modeling a large variety of OCT data from the fovea, and having a smaller root mean square error (RMSE) than other approaches, the method has difficulties deriving shape parameters relating to a 3D property of the fovea such as volume. Furthermore, the method is modeling the shape of the fovea not sufficiently accurate for allowing the differential diagnosis of the above mentioned diseases.

Liu et al. created a different 2D model, which uses a sloped piecemeal Gaussian function (SPG) to model the asymmetry and the foveal flatness [5]. The authors tested their method on a large number of macular scans and showed good RMSE compared to other 2D methods. The main drawback consists in the use of only two scans for each subject, a vertical and a horizontal one, which limits information to only these sections and prohibits generation of 3D metrics like volume.

Ding et al. developed an approach, which intends to model the surface of inner retinal layers using a 3D model-fit based DoG and a second order polynomial [1]. The authors used the model coefficients to discriminate between Parkinson patients and a control group. As a drawback, the model coefficients' relation to foveal shape itself is difficult to interpret. Additionally, although the model takes into account the difference in slope for horizontal and vertical directions, it does not model asymmetry in anatomical ones (temporal-nasal), nor does it capture fovea shapes with very flat pits accurately.

The problem is therefore to provide a method for accurate estimation of morphological features of the fovea that is capable to provide a representation of the fovea in three dimensions and that is particularly specific enough that a differential diagnosis between several neuroinflammatory diseases, particularly between NMO, MS, MOG and ON, can be made.

The problem according to the invention is solved by a method and a computer program for estimating shape parameters of three-dimensional volume data of a fovea, particularly acquired with optical coherence tomography.

Advantageous embodiments are described in the subclaims.

According to claim 1, a method for estimating a shape parameter of particularly three-dimensional image data of a fovea, particularly acquired with optical coherence tomography, comprises the steps of:

Acquiring an image data set, particularly a three-dimensional volume data set, of the fovea or the macula, comprising the foveal pit and the foveal rim, wherein the image data set is particularly acquired by optical coherence tomography, Estimating the center of the foveal pit, Estimating from the center of the foveal pit, radially extending height profiles of the fovea, particularly of the foveal pit, wherein the radially extending height profiles are particularly one-dimensional line profiles, For each height profile, fitting a model-function to the height profile, Estimating for each height profile a set of fit parameters from the fitted model-function, Estimating from the sets of estimated fit parameters at least one shape parameter of the fovea, particularly the foveal pit, Determining a shape or a shape feature of at least a part of the fovea, particularly of the foveal pit from the at least one shape parameter.

The steps indicated by bullet point need not necessarily be executed in the order written here, but if technically meaningful or even required the steps might be executed in a different order.

The determined shape or shape feature of at least a part of the fovea is particularly displayed on a display, such as a computer display, particularly in form of text or a graphical plot.

The shape features are particularly visualized such that a reconstruction of the foveal shape is achieved by the displayed or visualized shape features.

Due to the determination of the shape features, the method allows a more precise determination of morphological and/or topological features of the fovea, such that a more accurate description of the fovea can be achieved.

An image data set comprises the measurement data from the macula, particularly from the fovea. The image data set comprises particularly a three-dimensional volume data set that comprises measurement data along three dimensions, particularly along the x, y and z axis of a Cartesian coordinate system.

The data set particularly comprises pixels or voxels. In a volume data set a volume value, such as the signal intensity, is assigned to each voxel $(x_i, y_i, z_i)$ of the volume data set.

Such a three dimensional data set can for example consist of a stack of two-dimensional images of an image data set, wherein each two-dimensional image corresponds to a different position along the stack. For example a series of A- and B-scans of an OCT measurement can be assembled to a three-dimensional volume data set, wherein by means of an A-scan a depth profile can be displayed and by means of a B-scan a cross-sectional profile can be obtained.

The effective size of the three dimensional data set is chosen such that it fully comprises a region of the macula comprising the fovea, e.g. 6 mm×6 mm×6 mm, particularly with a resolution of at least 10 μm, more particularly of at least 4 μm.

Alternatively, it is possible to directly acquire an image data set that comprises or consists of a number of radial scans centered on the foveal pit. In this case obviously the estimation of the foveal pit precedes the acquisition step of the image data set.

The estimation of the radially extending height profiles is performed directly on the acquired image data set. In particular, the estimation of the radially extending height profiles is performed on a data set acquired from 3D macula cube scans. In other words the method according to the invention is used to generate a radial parametric model based on the 3D macula cube scans. In an alternative embodiment, the radial parametric model can be based on radial scans.

The estimation of the height profiles can be already comprised in the acquisition of the image data set. However, either pre-acquisition or post-acquisition, the center of the fovea as well as the height profiles are estimated at one point nonetheless, even though the image data set is acquired already such that it includes said steps. It is understood, that simultaneously performed steps of the method or execution of the method in a different order than the proposed order indicated by bullets, is within the scope of the invention, as the bullets explicitly do not indicate to a specific order or sequence of execution of the method according to the invention.

From such an image data set, it is possible to extract a macular thickness surface comprising for each point x, y of the surface data set a corresponding z-value, indicating the surface of the macular with respect to a reference layer, for example the lower boundary of the retinal pigment epithelium layer (RPE) as a reference level for the inner limiting membrane (ILM).

The determination of the macular thickness surface can be based on intensity values of the image data set. For segmentation of the ILM and/or RPE a variety of methods can be used.

For example, it is possible to extract the macular thickness surface by estimating the distance between the lower boundary of the RPE layer and the ILM. Both structures can be identified based on their OCT-signal values with suitable algorithms or by visual inspection.

The height-difference, i.e. the distance, between lower boundary of the RPE and ILM is particularly assigned as the macular thickness surface also referred to as the surface data set.

The estimation of the center of the foveal pit is particularly executed on the macular thickness surface data set. The center of the foveal pit is particularly the lowest point, i.e. the smallest distance between lower boundary of the RPE and ILM, of the macular thickness surface comprising the fovea. However, the center of the foveal pit can also be estimated by other means, such as for example by manual/visual estimation.

In a next step according to the invention, for example, the macular thickness surface is particularly segmented along radially extending directions, with the center of the foveal pit as the center of the radially extending segments.

In this step, the information acquired in the particularly three-dimensional volume data set is reduced to particularly line profiles along the macular thickness surface or the radially extending segments. These line profiles are referred to as height profiles or radial scans, as they could also be acquired directly by an accordingly configured OCT-recording system.

This step reduces the computational costs of fitting as the dimensionality of the fit problem is reduced. Also the complexity of the model-function can be greatly reduced by reducing the volume/surface data set to particularly one-dimensional radial height profiles.

Before the radial height profiles are generated, it is possible to radially re-sample the image data set or the surface data set such that the generated height profiles particularly have a higher data point density at the center of the foveal pit than on the outside of the foveal rim.

The re-sampling can also invoke an interpolation step, such as a bi-cubic or bi-linear interpolation. In contrast to interpolation, re-sampling comprises interpolation, thus a re-sampling step particularly comprises an interpolation step.

In order to achieve a sufficiently accurate description of the shape of the fovea, for each height profile a model-function is fitted independently to each height profile.

This model-function has to be configured to accurately match the respective radially extending height profile.

As the model-function comprises fit parameters that are adjusted in order to minimize or maximize an objective function, for each height profile a set of fit parameters can be estimated, once the model-function is fitted to the respective height profile.

From the fit parameters, at least one shape parameter of the fovea is estimated. The shape parameter can for example be or comprise a volume- or a surface-parameter, or a parameter describing a one-dimensional property of the fovea.

With the shape parameters it is possible to determine accurately a shape of at least a part of the fovea or the foveal pit. The term "shape" and "shape feature" also comprises a volume of the fovea or a part thereof.

A shape feature is particularly the corresponding feature that is described by the corresponding shape parameter. The shape of the fovea or parts of the fovea can be reconstructed by the determined shape features, i.e. the shape parameters.

It is particularly possible to reconstruct the macular thickness surface with high accuracy based on the fitted model-functions and the corresponding fit parameters.

According to another embodiment of the invention, the model-function comprises at least one Bézier function. It has been found that the Bézier function is particularly well-suited for accurately describing the shape of the radial height profiles of the fovea, the macular thickness surface or the ILM, respectively.

Particularly in contrast to other methods that aim to describe the shape of the fovea, the model-function comprising at least one Bézier function is capable to deliver an accurate and precise description of the fovea that particularly allows for the determination and differentiation between different pathological shapes of the fovea.

According to another embodiment of the invention, the model-function is fitted to the respective height profile with a least squares minimization algorithm.

The objective function (also referred to as the energy-function) for the least squares fit comprises the fit parameters and reflects the constraints and boundary conditions for fitting the model-function.

According to another embodiment of the invention, the model function is a Bézier function, particularly a cubic Bézier function or the model-function is or comprises a smooth composite Bézier path comprising Bézier functions, particularly cubic Bézier functions.

A smooth function in the context of the description is a function that is continuously differentiable at least once (C1-continuity).

A smooth composite Bézier path comprises a plurality of adjoining Bézier functions, wherein the Bézier functions are configured such at the adjoining points that the resulting composite Bézier path is smooth.

The shape of the radial height profiles can be described accurately by cubic Bézier functions, particularly by a smooth composite Bézier path, comprising Bézier functions that are of third order (cubic) only.

The fitting can be done sequentially for each Bézier function of the composite Bézier path with the appropriate connecting conditions or simultaneously, meaning that the Bézier functions are fitted in parallel.

According to another embodiment of the invention, the height profiles each comprise segments, wherein each segment is fitted with one of the Bézier functions, particularly with one of the cubic Bézier functions, comprised by the smooth composite Bézier path.

This embodiment provides a flexible way to provide a comparably simple model-function with comparably few degrees of freedom, wherein a good description of the height profiles is nonetheless achieved.

According to another embodiment of the invention, each height profile comprises an interior segment and an exterior segment, wherein the height profiles are fitted with the smooth composite Bézier path, wherein a first Bézier function, particularly a first cubic Bézier function, is fitted to the interior segment and wherein a second Bézier function, particularly a second cubic Bézier function, is fitted to the exterior segment, wherein the interior segment extends between a first end point and a second end point of the first Bézier function, and the exterior segment extends between a first end point and a second end point of the second Bézier function, wherein the second end point of the first Bézier function is identical to or adjoining with the first end point of the second Bézier function, wherein the first end point of the first Bézier function is at a first end of the height profile, particularly the center of the fovea, wherein the second end point of the first Bézier function and the first end point of the second Bézier function are at a maximum rim height of the height profile and the second end point of the second Bézier function is at a second end of the height profile, particularly wherein the first Bézier function has slope of zero at its first end point and wherein the first and second Bézier function have the same slope at the second end point of the first Bézier function and the first end point of the second Bézier function, wherein the slope is particularly zero at the second end point of the first Bézier function and the first end point of the second Bézier function.

The Bézier path with the first and second end points of the Bézier functions and the corresponding slope constraints provide just enough degrees of freedom to accurately fit the model-function to the respective height profile.

The maximum rim height is particularly the highest point of the respective radial height profile.

The slope at the second end point of the second Bézier function is particularly not predefined or constrained.

The distance between the second end point of the second Bézier function and the center of the fovea is fixed particularly between 1 mm and 3 mm, more particularly at 2 mm.

Control points associated to the respective end points are chosen or fitted accordingly such that the slope and shape of the Bézier path matches the height profile, the position of the control points are particularly adjusted by the fit algorithm.

According to another embodiment of the invention, each height profile is determined from a surface data set, wherein the surface data set comprises a distance between the ILM representing image data from the image data set and the lower boundary of the RPE representing image data from the image data set, wherein the radially extending height profiles are particularly one dimensional line profiles, or one-dimensional contours, extending along the respective radial direction of the surface data set.

As explained above, this step allows arriving at a surface data set that provides a reference layer, as the whole retina is comprised between the ILM and a lower boundary of the RPE. By using the distance between ILM and lower boundary of RPE it is possible to model the shape of the fovea in a generalized way applicable to all retina measurements. Feature of the fovea, in particular morphological features, can be determined such that a precise description of the fovea can be achieved.

This embodiment removes any ambiguity with regard to an inclination of the OCT-recording device and the eye. Furthermore the curvature of the retina is accounted for (compensated) in this embodiment.

According to another embodiment of the invention, the radially extending height profiles are regularly spaced, particularly with a spacing of 5° to 60°, more particularly with a spacing between 10° and 30°, even more particularly with a spacing of 15°.

The closer the spacing of the height profiles the more accurate the representation of the morphology of the fovea, but the higher the computational costs. A total number of height profiles between 12 and 36, particularly 24 is sufficient to obtain a sufficiently high accuracy for representing the morphology of the fovea. It is however also possible to acquire less than 12 height profiles, for example 6 height profiles only.

The height profiles particularly all adjoin at the foveal pit, particularly at the center of the foveal pit.

According to another embodiment of the invention, the at least one determined shape parameter of the fovea is one of the following, particularly reflecting one of the following morphological features of the fovea:

A central foveal thickness ($h_{cft}$),
An average rim height ($h_r$)
A rim disk area ($A_r$),
A minor axis and a minor axis length ($\lambda_2^r$) of the rim disk area ($A_r$),
A major axis and a major axis length ($\lambda_3^r$) of the rim disk area ($A_r$),
An average rim disk diameter ($d_r$),
An average pit depth ($h_p$),
An average maximum pit slope ($s_m$),
An average slope disk diameter ($d_s$),
A slope disk area ($A_s$),
A minor axis and a minor axis length ($\lambda_2^s$) of the slope disk area ($A_s$),
A major axis and a major axis length ($\Delta_3^s$) of the slope disk area ($A_s$),
A pit disk area ($A_f$),
A minor axis and a minor axis length ($\lambda_2^f$) of the pit disk area ($A_f$),
A major axis and a major axis length ($\lambda_3^f$) of the pit disk area ($A_f$),
An average pit disk diameter ($d_f$)
A rim volume ($V_r$),
An inner rim volume ($V_{IR}$), and/or
A pit volume ($V_p$).

All these shape parameters can be straight forwardly computed from the estimated fit parameters.

By means of the shape parameters, the shape of the fovea can be characterized such that a detailed description of the shape of the fovea by means of the shape parameters can be achieved.

The shapes of a plurality of foveae can be compared by means of respective shape parameters.

The variety of available shape parameters allows for searching correlations between specific diseases and specific (i.e. disease-correlating) sets of shape parameters.

The correlations between determined values or magnitude for specific shape parameters with specific diseases can be identified by a machine learning method, particularly with a trained classifier.

Here, particularly deviations of the magnitude of the at least one shape parameter can serve as a classification criterion. Also other variables can be taken into account by the trained classifier, such as age, sex and clinical data.

According to another embodiment of the invention, the image data is assigned to a morphological group, particularly based on the deviation or the magnitude of at least one determined shape parameter of the image data set, wherein the morphological group particularly comprises a plurality of selected shape parameters, wherein, particularly only if all shape parameters in the morphological group exhibit a predefined deviation (from a control set of parameters) or magnitude, the image data set is assigned to the morphological group.

Differential diagnosis particularly between MS and NMO and MOG and ON and other diseases, in particular neuroinflammatory diseases is therefore possible using the method according to the invention.

According to another embodiment of the invention, a first set of shape parameters associated to a first morphological group of the fovea comprises:

The minor axis length ($\lambda_2^s$) of the slope disk area ($A_s$),
The slope disk area ($A_s$), and
The average slope disk diameter ($d_s$).

This first set of shape parameters can be used for differential diagnosis for NMO as these parameters exhibit a sufficiently large deviation from a healthy control group (HC), when a patient suffers from NMO. Furthermore, these parameters exhibit said deviation from the HC independently of whether a NMO patient suffered from an optical neuritis (ON) or not.

Additionally, the shape parameters in the first group exhibit said deviations not for other diseases such as for example MS, or MOG, but are particularly altered only if the patient suffers from NMO.

The magnitude of deviation or the magnitude of the shape parameters for all morphological groups (also for the following) is particularly so large, that a probability of a false assignment is less than 10%, particularly less than 5%, more particularly less than 3%. Exemplary details of the magnitude of the expectable deviations are shown in the Figure and Example section.

According to another embodiment of the invention, a second set of shape parameters associated to a second morphological group of the fovea comprises:

The average rim height ($h_r$),
The major axis length ($\lambda_3^s$) of the slope disk area ($A_s$),
The pit disk area ($A_f$),
The average pit disk diameter ($d_f$),
The minor axis length ($\lambda_2^f$) of the pit disk area ($A_f$),
The inner rim volume ($V_{IR}$),
The average slope disk diameter ($d_s$).

This second set of shape parameters can be also used for differential diagnosis for NMO as these parameters exhibit a sufficiently large deviation from a healthy control group. However, in contrast to the shape parameters comprised in the first morphological group, these parameters exhibit said deviation also in dependence on a previously suffered ON. Thus, the changes in the shape parameters in the second group can be expected particularly only, if the patient has suffered from an ON prior the method according to the invention is performed on the patient.

According to another embodiment of the invention, a third set of shape parameters associated to a third morphological group of the fovea comprises:

The pit depth ($h_p$),
The major axis length ($\lambda_3^f$) of the pit disk area ($A_f$), and
The average maximum pit slope ($s_m$).

This third set of shape parameters is altered only by ON. Thus, the shape parameters comprised in the third group can be used for excluding other causes than a clinical ON.

According to another embodiment of the invention, a fourth set of shape parameters associated to a fourth morphological group of the fovea comprises:

The central foveal thickness ($h_{cft}$),
The average rim diameter ($d_r$),
The rim disk area ($A_r$), The major axis length ($\lambda_3^r$) of the rim disk area ($A_r$),
The minor axis length ($\lambda_2^r$) of the rim disk area ($A_r$),
The rim volume ($V_r$),
The pit volume ($V_f$), and
The inner rim volume ($V_{IR}$).

According to another embodiment of the invention, the acquired image data set is assigned to a morphological group, wherein the image data is assigned based on the value of at least one of the shape parameters, particularly by comparing the magnitude or deviation of the respective shape parameter to a predefined reference value for the shape parameter, particularly wherein the acquired image data set is assigned to the first morphological group based on the values of the shape parameters comprised in the first set of shape parameters, and/or particularly wherein the acquired image data set is assigned to the second morphological group based on the values of the shape parameters comprised in the second set of shape parameters, and/or particularly wherein the acquired image data set is assigned to the third morphological group based on the values of the shape parameters comprised in the third set of shape parameters.

According to another embodiment of the invention, a trained classifier, assigns the acquired image data set based on the value of at least one of the shape parameters, into a morphological group, particularly wherein the trained classifier assigns the acquired image data set based on the values of the shape parameters comprised in the first set of shape parameters to the first morphological group, and/or particularly wherein the trained classifier assigns the acquired image data set based on the values of the shape parameters comprised in the second set of shape parameters to the second morphological group, and/or particularly wherein the trained classifier assigns the acquired image data set based on the values of the shape parameters comprised in the third set of shape parameters to the third morphological group.

This embodiment allows for a computerized, i.e. automated distinction between different, particularly clinical morphological groups of the fovea.

By automatically assigning a data set to the respective morphological group, a decision support can be provided, when assessing the patients condition, with respect to the above mentioned diseases or inflammatory disorders.

Furthermore, the problem according to the invention is solved by a computer program, comprising computer program code, wherein when the computer program is executed on a computer, the computer program executes the method according to one of the preceding claims.

According to another embodiment of the invention, the acquired image data set is send from a computerized device to a server, wherein the acquired image data set is analysed by the computer program according to the invention, wherein the computer program is executed on the server, and a result of the analysed image data set is send to the computerized device. The result for example comprises the estimated at least one shape parameter of the fovea, particularly the foveal pit and/or an assigned the morphological group.

The terms 'processor' or 'computer', or system thereof, are used herein as ordinary context of the art, such as a general purpose processor or a micro-processor, RISC processor, or DSP, possibly comprising additional elements such as memory or communication ports. Optionally or additionally, the terms 'processor' or 'computer' or derivatives thereof denote an apparatus that is capable of carrying out a provided or an incorporated program and/or is capable of controlling and/or accessing data storage apparatus and/or other apparatus such as input and output ports. The terms 'processor' or 'computer' denote also a plurality of processors or computers connected, and/or linked and/or otherwise communicating, possibly sharing one or more other resources such as a memory. A server comprises at least one computer.

The terms 'computer program' or 'computer program code' denote one or more instructions or directives or circuitry for performing a sequence of operations that generally represent an algorithm and/or other process or method. The program is stored in or on a medium such as RAM, ROM, or disk, or embedded in a circuitry accessible and executable by an apparatus such as a processor, a computer or other circuitry.

The processor and program may constitute the same apparatus, at least partially, such as an array of electronic gates, such as FPGA or ASIC, designed to perform a programmed sequence of operations, optionally comprising or linked with a processor or other circuitry.

In the context of embodiments of the present disclosure, by way of example and without limiting, terms such as 'operating' or 'executing' imply also capabilities, such as 'operable' or 'executable', respectively.

According to another aspect of the invention the problem according to the invention is also solved by a method for diagnosing NMO and optic neuritis, wherein the method comprises the additional steps of:

Providing a set of reference shape parameters comprised in the first, second, and/or third morphological group, wherein said reference parameters are particularly determined from image data sets from a healthy control group (HC), Comparing the estimated shape parameters from the acquired image data set to the reference shape parameters, Estimating a deviation of the estimated shape parameters from the reference shape parameters, wherein, if the value of the shape parameters comprised in the first morphological group deviates by more than a predefined amount from the corresponding reference shape parameters, the acquired image data set is assigned NMO positive, wherein, if the value of the shape parameters comprised in the second morphological group deviates by more than a predefined amount from the reference shape parameters, and the patient has suffered from optical neuritis previously (ON), the acquired image data set is assigned NMO positive, wherein, if the value of the shape parameters comprised in the third morphological group deviates by more than a predefined amount from the corresponding reference shape parameters, the acquired image data set is assigned ON positive, particularly wherein, if the value of the shape parameters comprised in the fourth morphological group deviates by more than a predefined amount from the corresponding reference shape parameters, the acquired image data set is assigned to an unassigned group of health condition.

According to another embodiment of the invention, an additional diagnosis is performed on the person from which the image data set has been acquired and wherein the diagnosis method according to the invention is used complementary to the additional diagnosis method, particularly to verify or falsify the diagnoses result for the additional diagnoses method.

In the following Figure and Example section, the invention is explained in detail with reference to exemplary embodiments shown in the figures. It is noted that the drawings are not to scale.

1.1. Invariant Features of the Fovea

A retina 10 comprises different structures including the ILM 103, GCL 105 and RPE 104 and comprises the macula 50. The macula 50 comprises a fovea 100 wherein the fovea 100 comprises a foveal pit 101 and a foveal rim 102. The foveal rim 102 delimits the foveal pit 101 (FIG. 1). Foveal shape in the healthy population varies [10].

In FIG. 2, a selection of different foveal pit shapes from a cohort is shown to exemplify this. In particular, a fovea 100 comprising a large rim diameter (FIG. 2A), a small pit area (FIG. 2B), a flat pit (FIG. 2C), a big rim height (FIG. 2D), and an asymmetric pit (FIG. 2E) are shown. In order to reconstruct all these variations, invariant features of the foveal shape have to be identified. The tangents at critical points of the macula represent reliable and stable features. The critical points refer to the lowest point of the pit ($x_m$) and the highest point around this region ($x_1$, $x_2$) as shown in FIGS. 3A and 3B. The slope at these critical points is always zero and the macula will have horizontal tangents at these points.

1.2. Cubic Bézier

A parametric Bézier curve Q of polynomial degree n is defined as:

$$Q(t) = \sum_{i=0}^{n} P_{i,n} B_{i,n}(t), 0 \leq t \leq 1, \quad (1)$$

where the $P_{i,n}$ are the control points and $B_{i,n}$ are the Bernstein polynomials $$B_{i,n}(t) = \binom{n}{i} t^i (1-t)^{n-i}, i = [0, 1 \ldots, n]. \quad (2)$$

For a Bézier curve of degree n, there would be (n+1) control points. From Equation 1, it can be seen that the Bézier curve is a weighted average of the control points where weights are defined using the Bernstein polynomials. For n=3, Equation 1 becomes the cubic Bézier equation:

$$Q(t) = \sum_{i=0}^{3} P_i B_{i,3}(t), 0 \leq t \leq 1. \quad (3)$$

The cubic Bézier curve (also referred to as cubic Bézier function) has four control points and is tangent to the first and last control points $P_0$ and $P_3$ respectively [3]. The relationship between the control points, in terms of distance parameters α and β as well as unit tangent directions $T_{01}$ and $T_{23}$ can be written as:

The distance parameters α and β represent the distances between the end control point $P_1$-$P_0$=α·$T_{01}$, to as end points of the Bézier function, and the inner contractively $P_2$-$P_3$=−β·$T_{23}$. In the used curve fitting algorithm, the distance parameters α and β of each Bézier segment are used as shape parameters for an optimal curve fitting. The direction of a Bézier curve at its end points is uniquely determined by the tangent vector. Thus, by choosing the same tangent vector for two adjacent Bézier segments tangent continuity is assured, i.e. geometrical continuity $G^1$ at each junction, and thus throughout the whole composite spline curve.

1.3. Least Square Optimization

A least square fitting approach is used for each B-scan/radial scan using a cubic Bézier curve and the tangents at the critical points, derived from the invariant feature of the macular shape. c(x) is considered as the central B-scan which contains the minimal retinal thickness point as shown in FIG. 3A. The central B-scan can be decomposed into two interior ($c_1(x)$, $c_2(x)$) and two exterior ($c_0(x)$, $c_3(x)$) segments as shown in FIG. 3A.

The right half of the central B-scan is defined as the segment between the points ($x_m$, $c(x_m)$) and ($x_e$, $c(x_e)$) as shown in FIG. 3A. First, the maximum point of the right half of the central B-scan which is represented by ($x_2$, $c(x_2)$) is computed. Then, the right half segment is splitted into two segments at the critical point ($x_2$, $c(x_2)$) and each segment can be written as $c_I$: [$x_m$,$x_2$]→R for the interior and $c_E$: [$x_2$, $x_e$]→R for the exterior segment as shown in FIG. 3B. For the interior segment $c_I$, the end points $P_0$ and $P_3$ have the horizontal tangent lines T=[1, 0] and the inner control points $P_1$ and $P_2$ are lying opposite to each other with respect to their tangent direction, as shown in FIG. 3B (left part). So, Equation 4 can be modified as:

$$P_1 = P_0 + \alpha \cdot T, P_2 = P_1 - \beta \cdot T. \quad (5)$$

For the exterior segment $c_E$ of the macula (FIG. 3B, right part), only one of the end points has the horizontal tangent and one of the inner control point $P_1$ lies in the same horizontal tangent direction. Equation 4 can be modified for the exterior segments of the fovea to:

$$P_1 = P_0 + \alpha \cdot T. \quad (6)$$

The other inner control point $P_2$ for the exterior segment does not have the horizontal tangent direction (T=[1, 0]), therefore the value of $P_2$ is optimized without using any invariant feature of the macula. In the proposed method, the control points $P_i$ are defined in $R^2$ space. In the next step, the optimized values of α and β are computed for a best fitting the cubic Bézier function for each segment of the corresponding scan. The optimization process begins from the interior segment. By using Equation 3 and 5, the cubic Bézier equation is modified for the interior segment $c_I$ as follows:

$$Q_I(t,\alpha,\beta) = \alpha TB_1(t) - \beta TB_2(t) + P_0(B_0(t) + B_1(t)) + P_3(B_2(t)) + P_3(B_2(t) + B_3(t)). \quad (7)$$

If the corresponding segment has m data points and is represented by $D^I$ then the least square energy function is expressed as:

$$E(t, \alpha, \beta) = \sum_{i=1}^{m} \|D_i^I - Q_I(t_i, \alpha, \beta)\|^2. \quad (8)$$

Equation 8 shows a quadratic energy function which is a convex energy function and has a unique minima. The minimization of the above energy function will become the multi-space optimization because the three different variables have to be minimized. The multi-space optimization procedure for t, α and β are explained in the following two steps:

1. An initial value is given to $t \in [0, 1/m, 2/m, \ldots, 1]$ using the uniform parametrization and the corresponding α and β are calculated by computing the first derivative of the given energy function with respect to α and β

$$\nabla_\alpha E = 0, \nabla_\beta E = 0. \tag{9}$$

The gradient of the given energy w.r.t α is computed:

$$\nabla_\alpha E = 2\sum_{i=1}^{m}(D_i^I - Q_I(t_i, \alpha, \beta)) \cdot B_1(t) \cdot T, \tag{10}$$

by using Equation 9, the following relation is concluded:

$$\sum_{i=1}^{m} B_1(t) \cdot Q_I(t_i, \alpha, \beta) = \sum_{i=1}^{m} D_i^I \cdot B_1(t), \tag{11}$$

where the left hand side of the above equation will have only α as the unknown variable, because the terms which are consisting β will be omitted due to the differential operation. Similarly, β can be computed using Equation 9.

2. In the next step, the optimized value of t is computed using the following equation with the values α and β computed at the previous step.

$$\nabla_t E = 0. \tag{12}$$

The derivate of the given energy function w.r.t. t is computed:

$$\nabla_t E = -2\sum_{i=1}^{m}(D_i^I - Q_I(t_i, \alpha, \beta)) \cdot Q_I'(t_i, \alpha, \beta), \tag{13}$$

where $Q'^I(t_i, \alpha, \beta)$ represents the first derivative of cubic Bézier with respect to t. Equation 12 and 13 can be solved either by the linear system equation or by using the gradient descent. In the algorithm, the gradient descent method is used to compute the optimized value of t. These two steps are iterated until the minima of the convex energy function in the Equation 8 are determined. In the experiment, the minima of the given energy can be achieved in 400 iterations. After 400 iterations, there is no significant change in the optimization result.

For the exterior segment $c_E$, the optimization procedure will be different compared to the interior segments because only one end point has the horizontal tangent. Using Equation 6, Equation 3 is modified:

$$Q_E(t, P_2, \alpha) = \alpha T B_1(t) + P_0(B_0(t) + B_1(t)) + P_2 B_2(t) + P_3 B_3(t)). \tag{14}$$

Similar to the energy function in Equation 8, another energy function can be defined $$E(t, P_2, \alpha) = \sum_{i=1}^{m} \left\| D_i^E - Q_E(t_i, P_2, \alpha) \right\|^2, \tag{15}$$

where $D^E$ represents the data points corresponding to the external segment. The minimization of this given function will be done similar to the interior segment parameter optimization. In the first step, the derivative of the energy function with respect to $P_2$ and α for a given initial uniform parameterized t is computed. Then, in the next step, the optimized t with the newly obtained values for $P_2$ and α is computed.

2.1 Materials and Methods

To evaluate the method described in the present specification macular volume scan (25°×30°, 61 vertical or horizontal B-scans, 768 A-scans per B-scan, with each B-scan being the result of 9-15 averaged B-scans) captured with the Spectralis OCT (Heidelberg Engineering, Heidelberg, Germany) are used. The voxel dimensions in the horizontal, axial directions and distance between B-scans in this data set were approximately 11.69, 3.87, and 125 m respectively. A total of 187 OCT scans, 95 from healthy controls (HC) and 92 from patients with different autoimmune neuroinflammatory diseases, were selected from the NeuroCure Clinical Research Centers' imaging database. All scans underwent quality control by an experienced rater. Automatic layer segmentation was performed with the device's software (Eye Explorer 1.9.10.0 with viewing module 6.0.9.0). The imaging database only contains images derived from local studies that were approved by the local ethics committee at the Charité-Universitätsmedizin Berlin and were conducted following the Declaration of Helsinki in its currently applicable version. All computations were carried out using MATLAB 2016b (MathWorks, Inc., Natick, Mass., USA). The statistical analysis was conducted using R version 3.3.2 [4]. ICC (inter class correlation) and GEE (Generalized estimating equation) is used for the statistical measurement. The ICC measures the repeatability of the proposed parameters and GEE (p-value) shows the significance between the two groups of data for each of the proposed parameters.

3.1 Method Pipeline

FIG. 4 shows the pipeline of one embodiment of the invention. In order to import the data into MATLAB, Heidelberg Spectralis OCT raw data format was exported from the device. This data contains additional to the image information, the coordinates of the inner limiting membrane (ILM) and the lower boundary of the retinal pigment epithelium layer hereafter also referred to as RPE. The whole method is implemented in following steps:

3.2 ILM-RPE Computation and Minimal Foveal Point Detection

In the first step, the height difference between the ILM and the RPE of each volume scan is extracted. This represents the macular thickness surface. Using this difference has the advantage of removing the slant of the scan created at the measurement and/or by the curved shape of the eye. A volume scan and the corresponding thickness profile is represented as the graph function M: $(x,y) \rightarrow R$, where $(x,y) \in \Omega$ and $\Omega$ represents a region of interest. A volume scan is the combination of A-scans and B-scans obtained from the OCT scanner. x and y represent A-scans and B-scans directions, respectively. To determine the fovea's center, a region 12 of 1 mm radius is taken from this surface centered at the fovea automatically detected by the OCT device. The information about this center point is included in the raw data export. In order to detect the lowest point of the foveal surface, the minima of this region are determined.

$$M_m = M(x_m, y_m), \tag{16}$$

where $x_m$, $y_m$ are the coordinate of the minimum value $M_m$ of the volume scan. If several minima are detected, then the median point of them is taken as the center of the foveal pit.

3.3 Volume to Radial Sampling

The second step of the method is directed towards a volume to radial sampling (FIG. 4). For 3D shape analysis of the fovea, the information from the whole volume is needed, and therefore the scan is re-sampled into a radial one. The radial scans capture the foveal pit shape accurately as they have more samples near to the center compared to the outer region of the fovea. The sampling from volume M to radial $M_p$ can be done in following steps:

(a) A polar grid $Mp(r,\theta)$ is created, and centered at the $(x_m, y_m)$ with zero height value. The radius and the angle between the radial lines can be defined by the user.

(b) The height value of $Mp(r, \theta)$ is computed, using the bilinear interpolation between the nearest four points of the $M(x,y)$ which are closest to the corresponding $(r, \theta)$.

(c) Now, $n=(2\pi, \theta)$ radial scans can be represented as:

$$c(r,\theta_i) \in M_p(r,\theta) \text{ where } i=1, \ldots, n.$$

These radial scans (white lines) approximate the original volume scan (dark area) as shown in FIG. 5A.

In the disclosed examples r=2 mm and $\theta=15°$ for the radial sampling was chosen.

3.4 Segmentation of the Radial Scans

Each of the radial scan $(r, \theta_i)$, is segmented into interior $c_I$ and exterior $c_E$ regions at the corresponding maximum (critical) point, as shown in FIG. 3B.

3.5 Cubic Bézier Fitting Using Least Square Optimization

For each of the segments of the radial scan, a cubic Bézier function with the least square optimization was fitted, as explained in section 1.3.

For the interior segment, Equation 8, 9 and 12 are used to compute optimized a, p and t. Then, the interior segment was reconstructed using the optimized parameters by assigning these to Equation 7. Similarly, for exterior segment, Equation 15 is used to compute optimized a, $P_2$ and t. Then the exterior segment is reconstructed using Equation 14. To get a complete 3D parameterized modeling of the fovea, a cubic Bézier function is fitted to each of the re-sampled radial scans. FIG. 5B shows the 3D-parameterized model with 24 radial scans. Each line of white circles corresponds to each one white line shown in FIG. 5A, each line of black circles represents a corresponding fit. The large black circular rings show the critical points for each radial scan.

3.6 Parameters Computation

By using the parameterization of the fovea, several parameters for the volume scan are computed. The analytical formulations of these parameters are shown in the next section.

4. Parameters

In this section, several shape parameters for a volume scan using a cubic Bézier parameterization are presented. A rim point of a radial scan is defined as the maximum height point in the corresponding radial scan.

There are n number of radial scans re-sampled from a volume scan and $(p_1, p_1, \ldots, p_n) \in R^3$ are the corresponding rim points. FIG. 6A and FIG. 6B show re-sampled radial scans from a volume scan divided in two parts: $c(r, \theta_i)$ and $c(r, \theta_i+\pi)$ The notation used to denote the corresponding least square optimization fitted radial scan parts is $Q(t, \theta_i)$ and $Q(t, \theta_i+\pi)$, respectively, for all i=1, . . . , n. A visual representation of some of the 3D parameters is shown in FIGS. 8A and 8B as well as FIGS. 9A to 9D. FIG. 7 shows two parameterized radial scans $(Q(t, \theta_i)$ and $Q(t, \theta_i+\pi))$ of a volume scan which differ by the angle $\pi$. Several basic parameters are defined based on these two radial scans. $Q_I$ and $Q_E$ represent parameterized interior and exterior segments respectively. Most of the 3D parameters are computed by first computing the values for each radial scans and then taking the average over these scans.

4.1 Central Foveal Thickness ($h_{cft}$)

is defined as the minimum height of the fovea at the center of the pit (FIG. 7). From Equation 16, $h_f$ can be written as:

$$h_{cft}=M(x_m,y_m). \quad (17)$$

The $h_{cft}$ of each radial scan will be same because $(x_m, y_m)$ is the center of radial and represents the beginning as well as the lowest point for each radial scan.

4.2 Average Rim Height ($h_r$)

is defined as the average of the maximum height in each radial scan of a volume (as shown in FIGS. 3A and 3B, FIG. 7). Average rim height is written as:

$$h_r = \frac{1}{n}\sum_{i=1}^{n}\max(c(r, \theta_i)). \quad (18)$$

4.3. Rim Disk Area ($A_r$)

To compute the rim disk area, the normal to the disk plane as shown in FIGS. 8A and 8B is computed. The covariance analysis of all the rim points provides not only the disk normal but also shape information as described below. Rim points covariance matrix $C_r$ can be computed as:

$$C_r = \frac{1}{n}\sum_{i=1}^{n}(p_c - p_i)^T(p_c - p_i), \quad (19)$$

$$p_c = \frac{1}{n}\sum_{i=1}^{n}p_i.$$

Eigen analysis of the matrix $C_r$ provides shape information about the rim disk. The vector $\lambda=[\lambda_1, \lambda_2, \lambda_3]$ represents the eigenvalues sorted in decreasing order: $\lambda_1 \geq \lambda_2 \geq \lambda_3$ and $[\upsilon_1, \upsilon_2, \upsilon_3]$ are the corresponding eigenvectors. The most dominant eigenvalues $\lambda_1$ and $\lambda_2$, represent the Major and the Minor axis of the rim disk, respectively. The least dominant eigen direction will be the disk normal so $n_p=\upsilon_3$. Now, the Rim Disk Area $A_r$ can be computed as:

$$A_{3D} = \frac{A_{2D}}{\cos\theta}, \theta = \angle(n_p, n_z), \quad (20)$$

where $n_z=[0, 0, 1]$ and $A_{2D}: R^2 \rightarrow R$ is the area of the projection of the $A_{3D}$ on XY-plane (see FIG. 8B).

4.4 Average Rim Disk Diameter ($d_r$)

$p_{\theta_i}$ and $p_{\theta_{i+\pi}}$ are two rim points corresponding to the two parameterized opposite radial scans ($Q(t, \theta_i)$ and $Q(t, \theta_i+\pi)$, respectively). The average rim diameter is written as:

$$d_r = \frac{2}{n}\sum_{i=1}^{n/2} \|p_{\theta_i} - p_{\theta_{i+\pi}}\|. \tag{21}$$

4.5 Average Pit Depth ($h_p$)

represents the depth of the foveal pit and can be computed as the difference between the average rim height ($h_r$) and central foveal thickness ($h_{cft}$):

$$h_p = h_r - h_{cft}. \tag{22}$$

4.6 Average Maximum Pit Slope ($s_m$)

Average maximum pit slope measures the steepness of the foveal pit. It is defined as the average of the maximal slope of each radial scan. The slope of a parameterized radial scan $Q(r, \theta_i)$ is defined as:

$$s_i = \frac{dQ_I^y(t)/dt}{dQ_I^x(t)/dt}$$
$$i = 1, \ldots, n,$$

where $Q_I^y(t)$ and $Q_I^x(t)$ represent parameterized x and y coordinates for the interior segment. To calculate the maxima of the above equation, the gradient, $\nabla_{tSi}=0$ is computed and the value of $t_{mi}$ for the maximal slope ($s_{mi}$) is achieved:

$$s_{m_i} = \frac{P_3^y - P_0^y}{\alpha - \beta - \sqrt{\alpha\beta} - (P_3^x - P_0^x)}, \tag{23}$$

$$t_{m_i} = \frac{\sqrt{\alpha}}{\sqrt{\alpha} + \sqrt{\beta}},$$

where $P_3^y(t)$ and $Q_3^x(t)$ are the y coordinates of the end control points of $Q_1(t, \theta_i)$. Similarly, $P_3^x$ and $P_0^x$ are the x coordinates of the end control points of $Q_I(t, \theta_i)$. The average maximum pit slope of a volume is defined as:

$$s_m = \frac{1}{n}\sum_{i}^{n} s_{m_i}. \tag{24}$$

4.7 Average Slope Disk Diameter ($d_s$)

Average slope disk diameter is computed similar to the average rim diameter $d_r$. Slope width is computed between two opposite parameterized radial scans: $Q(t, \theta_i)$ and $Q(t, \theta_i+\pi)$ and the corresponding maximum slope points are $p_{\theta_i}^s$ and $p_{\theta_{i+\pi}}^s$ such that:

$$p_{\theta_i}^s(x)=Q^x(t_m,\theta_i),\ p_{\theta_i}^s(x)=Q^x(t_m,\theta_i),\ p_{\theta_{i+\pi}}^s(x)=Q^x(t_m,\theta_i+\pi),\ p_{\theta_{i+\pi}}^s(x)=Q^y(t_m,\theta_i+\pi), \tag{25}$$

where $t_m$ represents maximum slope point in parametric domain as shown in Equation 23 and $Q^x(t_m, \theta_i)$, $Q^Y(t_m, \theta_i)$ are the corresponding x and y coordinate. Average slope width of a volume is defined as:

$$d_s = \frac{2}{n}\sum_{i=1}^{n/2}\|p_{\theta_i}^s - p_{\theta_{i+\pi}}^s\|. \tag{26}$$

4.8 Slope Disk Area ($A_s$)

The slope disk area can be computed similar to the rim disk area. $(p_1^s, p_2^s, \ldots, p_n^s) \in R^3$ are the maximum slope points corresponding to the each radial scan and are computed using the Equation 23 and 25. Covariance of maximal slope points can be computed using Equation 19 to obtain the normal vector, major and minor axes of the slope disk.

4.9 Pit Flat Disk Area ($A_f$)

The pit flat disk area measures the flatness of the foveal pit around the center and is computed using a threshold value $\tau$ for each of the radial scans. In each radial scan, a point $p_{\theta_i}^f$ is computed, where the retinal thickness is smaller than $\tau$. Then the corresponding segment from the center ($x_m$, $y_m$) to the computed point $p_{\theta_i}^f$ is treated as flat. This can be done in following two steps:

1. The parametric value $t_f$ corresponding to the threshold value $\tau$ is computed:

$$\tau - Q_I^y(t_f,\theta_i)=0. \tag{27}$$

2. The x value corresponding the parameterized value $t_f$ is computed:

$$d_{fi} = Q_E^x(t_f,\theta_i). \tag{28}$$

The point $p_{\theta_i}^f=(d_{si}, \tau, \theta_i)$ corresponds to the pit flat point for a single radial scan. Similarly, $(p_1^f, p_2^f, \ldots, p_n^f) \in R^3$ can be considered as the pit flat points. The area, major and minor axis of the pit flat disk can be computed similar to the rim disk area. The Average Pit Flat Disk Diameter ($d_f$) using $d_{fi}$ from Equation 28 can be computed:

$$d_f = \frac{2}{n}\sum_{i=1}^{n} d_{f_i}. \tag{29}$$

4.10 Rim Volume ($V_r$)

In general, the volume under a surface in Cartesian and Polar domains can be computed using the following equation:

$$V_r = \iint_A f(x,y)dxdy = \int_0^{2\pi}\int_0^R c(r,\theta)rdrd\theta.$$

After the discretization process of the whole volume into n radial directions, the above equation will become:

$$V_r = \frac{2\pi}{n}\sum_{i=1}^{n}\int_0^R c(r, \theta_i)rdr.$$

The above equation is modified using the following substitution. The interior parameterized curve $Q_I(t, \theta_i)$ is defined between the center and the rim points. So the parametric value $t \to \{Q_I^X(t, \theta_i), Q_I^Y(t, \theta_i)\}$ will be t=0 and t=1 at the center and the rim points, respectively.

Similarly, $r = Q_I^X(t, \theta_i)$, $Q_I^Y$, $R = Q_I^X(1, \theta_i)$, $C(r, \theta_i) = Q_I^Y(1, \theta_i)$ and $$dr = \frac{dQ_I^X(t, \theta_i)}{dt} dt.$$

After the substitution, the rim volume can be written as:

$$V_r = \frac{2\pi}{n} \sum_{i=1}^{n} \int_0^1 Q_I^y(t, \theta_i) Q_I^x(t, \theta_i) \frac{dQ_I^x(t, \theta_i)}{dt} dt. \quad (30)$$

In the above equation, $R = P_3^x$ and at the end point of the parametric curve t is equal to 1. R might have different values for different radial scans because of an asymmetry of the foveal pit.

4.11 Inner Rim Volume ($V_{IR}$)

Inner rim volume is defined as the volume of the fovea within the fixed radius from the center. The radius is given by the user. $t_u$ is the parametric value corresponding to the user input radius $r_u$ for each radial direction. Equation 30 can be modified:

$$V_{IR} = \frac{2\pi}{n} \sum_{i=1}^{n} \int_0^{t_u} Q_I^y(t, \theta_i) Q_I^x(t, \theta_i) \frac{dQ_I^x(t, \theta_i)}{dt} dt. \quad (31)$$

Before using the above equation, one has to make sure that the radius R will be equal to the minimum of the $P_3^x$ from all the radial directions. In case, R is bigger than any of the $P_3^x$, one needs to introduce the exterior segment into the integration as well.

4.12 Pit Volume ($V_p$)

The total volume ($V_t$) under the rim disk, $V_t = A_{3D} h$ is calculated, where h is the average height of the rim points. Then, the pit volume can be defined as:

$$V_p = V_t - V_r. \quad (32)$$

Table 1: Normative values for healthy controls. Macula scans of 423 eyes of 218 subjects of Caucasian descent were included, from which 144 (66%) were females and 74 (34%) were males. Age was between 18.07 and 68.93 years, with an average (+/−standard deviation (STD)) of 36.5 (+/− 12.27). The sample size of the healthy controls cohort has similar age and sex distribution to the cohorts of autoimmune neuroinflammatory diseases, i.e. Multiple Sclerosis, NMO. This characteristic makes it an appropriate reference database in studies with these diseases.

In Table 1A, parameters for the healthy control group (All) are given. In Table 1B and Table 1C, parameters for a subgroup exclusively comprising data from female donors (female) and for a subgroup exclusively comprising data from male donors (male), respectively, are given. Mean values (Mean) and standard deviations (STD), the minimal (Min) and maximal (Max) values are given.

TABLE 1A

| Parameters | All Mean(+/− STD) | All Min | All Max |
|---|---|---|---|
| Avg_Pit_Depth_mm | 0.13(+/−0.02) | 0.0482 | 0.1688 |
| Central_Foveal_Thickness_mm | 0.2306(+/−0.0181) | 0.1918 | 0.3014 |
| Average_Rim_Height_mm | 0.3606(+/−0.0134) | 0.3235 | 0.4042 |
| Average_Rim_Diameter_mm | 2.1776(+/−0.2191) | 1.5128 | 2.7458 |
| Rim_Disk_Area_mm2 | 3.7459(+/−0.7503) | 1.8114 | 5.9123 |
| Major_Rim_Disk_Length_mm | 0.6529(+/−0.1331) | 0.3267 | 1.0592 |
| Minor_Rim_Disk_Length_mm | 0.5558(+/−0.1112) | 0.2556 | 0.8902 |
| Major_Slope_Disk_Length_mm | 0.0585(+/−0.0257) | 0.0184 | 0.1828 |
| Minor_Slope_Disk_Length_mm | 0.0495(+/−0.0222) | 0.0132 | 0.1559 |
| Slope_Disk_Area_mm2 | 0.3407(+/−0.1495) | 0.1083 | 1.0524 |
| Average_Slope_Disk_Diameter | 0.6333(+/−0.1381) | 0.3286 | 1.1476 |
| Pit_Disk_Area_mm2 | 0.0295(+/−0.0125) | 0.0099 | 0.0894 |
| Average_Pit_Flat_Disk_Diameter | 0.1866(+/−0.0381) | 0.1061 | 0.3335 |
| Major_Pit_Flat_Disk_Length_mm | 0.0051(+/−0.0022) | 0.0017 | 0.015 |
| Minor_Pit_Flat_Disk_Length_mm | 0.0042(+/−0.0018) | 0.0014 | 0.0134 |
| Rim_Volume_mm3 | 0.9497(+/−0.1922) | 0.4544 | 1.4896 |
| Pit_Volume_mm3 | 0.4009(+/−0.082) | 0.189 | 0.639 |
| Inner_Rim_Volume_mm3 | 0.0757(+/−0.0124) | 0.0423 | 0.1242 |
| Avg_Max_Pit_Slope_deg | 12.4694(+/−2.583) | 4.6204 | 20.8299 |

TABLE 1B

| Parameters | Female Mean(+/−STD) | Female Min | Female Max |
|---|---|---|---|
| Avg_Pit_Depth_mm | 0.1288(+/−0.0188) | 0.0768 | 0.1664 |
| Central_Foveal_Thickness_mm | 0.2293(+/−0.0167) | 0.1918 | 0.2949 |
| Average_Rim_Height_mm | 0.3581(+/−0.0127) | 0.3235 | 0.4042 |
| Average_Rim_Diameter_mm | 2.188(+/−0.2172) | 1.5128 | 2.7342 |
| Rim_Disk_Area_mm2 | 3.7809(+/−0.7502) | 1.8114 | 5.9123 |
| Major_Rim_Disk_Length_mm | 0.657(+/−0.1328) | 0.3267 | 1.0592 |
| Minor_Rim_Disk_Length_mm | 0.5628(+/−0.1113) | 0.2556 | 0.8735 |
| Major_Slope_Disk_Length_mm | 0.0611(+/−0.0267) | 0.0198 | 0.1828 |
| Minor_Slope_Disk_Length_mm | 0.0518(+/−0.023) | 0.0163 | 0.1559 |
| Slope_Disk_Area_mm2 | 0.3562(+/−0.1553) | 0.1154 | 1.0524 |
| Average_Slope_Disk_Diameter | 0.6479(+/−0.1399) | 0.3705 | 1.1476 |
| Pit_Disk_Area_mm2 | 0.031(+/−0.0126) | 0.0105 | 0.0894 |
| Average_Pit_Flat_Disk_Diameter | 0.1917(+/−0.038) | 0.1127 | 0.3335 |
| Major_Pit_Flat_Disk_Length_mm | 0.0054(+/−0.0022) | 0.0018 | 0.015 |
| Minor_Pit_Flat_Disk_Length_mm | 0.0045(+/−0.0019) | 0.0014 | 0.0134 |
| Rim_Volume_mm3 | 0.9532(+/−0.1917) | 0.4544 | 1.4767 |
| Pit_Volume_mm3 | 0.4009(+/−0.0809) | 0.189 | 0.6076 |
| Inner_Rim_Volume_mm3 | 0.0743(+/−0.012) | 0.0423 | 0.1237 |
| Avg_Max_Pit_Slope_deg | 12.3188(+/−2.4894) | 7.0278 | 20.4275 |

TABLE 1C

| Parameters | Male Mean(+/−STD) | Male Min | Male Max |
|---|---|---|---|
| Avg_Pit_Depth_mm | 0.1323(+/−0.022) | 0.0482 | 0.1688 |
| Central_Foveal_Thickness_mm | 0.233(+/−0.0204) | 0.1994 | 0.3014 |
| Average_Rim_Height_mm | 0.3654(+/−0.0134) | 0.3327 | 0.4002 |
| Average_Rim_Diameter_mm | 2.1573(+/−0.222) | 1.6047 | 2.7458 |
| Rim_Disk_Area_mm2 | 3.678(+/−0.7485) | 2.0344 | 5.8958 |
| Major_Rim_Disk_Length_mm | 0.6448(+/−0.1338) | 0.3484 | 1.0182 |

TABLE 1C-continued

| Parameters | Male Mean(+/−STD) | Male Min | Male Max |
|---|---|---|---|
| Minor_Rim_Disk_Length_mm | 0.542(+/−0.11) | 0.8902 | 0.2923 |
| Major_Slope_Disk_Length_mm | 0.0535(+/−0.023) | 0.1251 | 0.0184 |
| Minor_Slope_Disk_Length_mm | 0.045(+/−0.0198) | 0.0132 | 0.1025 |
| Slope_Disk_Area_mm2 | 0.3106(+/−0.133) | 0.1083 | 0.7084 |
| Average_Slope_Disk_Diameter | 0.6051(+/−0.1302) | 0.3286 | 0.9482 |
| Pit_Disk_Area_mm2 | 0.0264(+/−0.0116) | 0.0099 | 0.0828 |
| Average_Pit_Flat_Disk_Diameter | 0.1768(+/−0.0365) | 0.1061 | 0.3209 |
| Major_Pit_Flat_Disk_Length_mm | 0.0046(+/−0.002) | 0.0017 | 0.0147 |
| Minor_Pit_Flat_Disk_Length_mm | 0.0038(+/−0.0017) | 0.0014 | 0.0118 |
| Rim_Volume_mm3 | 0.943(+/−0.1937) | 0.5064 | 1.4896 |
| Pit_Volume_mm3 | 0.401(+/−0.0842) | 0.2054 | 0.639 |
| Inner_Rim_Volume_mm3 | 0.0785(+/−0.0127) | 0.0546 | 0.1242 |
| Avg_Max_Pit_Slope_deg | 12.7613(+/−2.7408) | 4.6204 | 20.8299 |

TABLE 2

Repeatability test for the 3D parameters. Abbreviations: ICC - intra-class correlation coefficient; LCI - lower confidence interval; UCI - upper confidence interval.

| Parameters | ICC | LCI | UCI |
|---|---|---|---|
| Avg. Pit Depth ($h_p$) (mm) | 0.981 | 0.966 | 0.990 |
| Central Foveal Thickness ($h_{cft}$) (mm) | 0.989 | 0.980 | 0.994 |
| Avg. Rim Height ($h_r$) (mm) | 0.976 | 0.957 | 0.987 |
| Avg. Rim Disk Diameter ($d_r$) (mm) | 0.925 | 0.868 | 0.960 |
| Rim Disk Area ($A_r$) (mm$^2$) | 0.919 | 0.858 | 0.957 |
| Major Axis Rim Disk ($\lambda_3^r$) (mm) | 0.909 | 0.843 | 0.952 |
| Minor Axis Rim Disk ($\lambda_2^r$) (mm) | 0.906 | 0.838 | 0.950 |
| Avg. Slope Disk Diameter ($d_s$) (mm) | 0.930 | 0.878 | 0.963 |
| Slope Disk Area ($A_s$) (mm$^2$) | 0.946 | 0.905 | 0.972 |
| Major Axis Slope Disk ($\lambda_3^s$) (mm) | 0.936 | 0.888 | 0.966 |
| Minor Axis Slope Disk ($\lambda_2^s$) (mm) | 0.946 | 0.905 | 0.972 |
| Avg. Pit Flat Disk Diameter ($d_f$) (mm) | 0.896 | 0.821 | 0.945 |
| Pit Flat Disk Area ($A_f$) (mm$^2$) | 0.915 | 0.852 | 0.955 |
| Major Pit Flat Disk Length ($\lambda_3^f$) (mm) | 0.899 | 0.825 | 0.946 |
| Minor Pit Flat Disk Length ($\lambda_2^f$) (mm) | 0.913 | 0.849 | 0.954 |
| Rim Volume ($V_r$) (mm$^3$) | 0.895 | 0.820 | 0.944 |
| Inner Rim Volume ($V_{IR}$) (mm$^3$) | 0.966 | 0.940 | 0.983 |
| Pit Volume ($V_p$) (mm$^3$) | 0.960 | 0.929 | 0.979 |
| Avg. Max. Pit Slope ($s_m$) (Degrees) | 0.969 | 0.945 | 0.984 |
| $\alpha_m$ (mm) | 0.917 | 0.855 | 0.956 |
| $\beta_m$ (mm) | 0.810 | 0.686 | 0.896 |

5. Experiments. Results and Discussion

Scans from 187 eyes consisting of 95 eyes of a healthy control group (healthy eyes) and 92 eyes from patients with autoimmune neuroinflammatory diseases (with and without previous optic neuritis) were processed. The implementation of the method according to the invention is quite straight forward and follows the pipeline mentioned in section 3.1 (c.f. FIG. 4). The method according to the invention is implemented in a single computation thread and it takes around 3 seconds to compute the parametric 3D model and related parameter on a standard PC.

For the healthy control group, the 3D normative parameters have been determined (Table 1). The mean values and standard deviations, the minimal and maximal values are given for the entire healthy control group ("All", Table 1A), for a subgroup exclusively comprising data from female donors ("female", Table 1B) and for a subgroup exclusively comprising data from male donors ("male", Table 1C).

5.1 Re-Test Reliability

The method according to the invention is able to successfully model all scans; visual inspection of model results did not suggest modelling failure in any of the included scans. Table 2 shows test-retest reliability applied to a group of data including three repeated measurements of 30 healthy eyes. Intra-class correlation coefficient (ICC) for the 3D derived parameters varied from 0.8102 for $\beta_m$ to 0.9894 for central foveal thickness ($h_{cft}$) as shown in Table 2. From Table 2, $\beta_m$ has the lowest repeatability. Basically, $\alpha_m$ and $\beta_m$ are the average of all $\alpha$ and $\beta$ belonging to radial scans of the interior region of the fovea. As mentioned in Equation 5, $\alpha$ and $\beta$ represent the distance between the control points $P_0$, $P_1$ and $P_3$, $P_2$, respectively. The low ICC value obtained for $\beta_m$ indicates that the distance between the $P_3$ and $P_2$ is not consistent. Perhaps, the small inaccuracy in rim point detection is leading to the low repeatability of $\beta_m$. On the other hand, a depends on the center or beginning control point ($P_0$) which is fix for a volume scan. Therefore, $\alpha_m$ has a better repeatability compared to $\beta_m$.

5.2 Model Accuracy

For root-mean-square-error (RMSE) comparison, two state-of-the-art methods for foveal shape analysis have been implemented, the one proposed by Ding et al. [1], and the one described in Dubis et al. [2] and have been compared with the method according to the invention. For a better readability, [1] is referred to as M1 and [2] is referred to as M2. In case of M1 the 3D approach was implemented, as presented in the paper [1]. For M2 the 3D version was implemented by extending the 2D method presented by the authors to the radial re-sampled volume. In order to visualize the behavior of M1 vs. M2 vs. the method according to the invention, the fitting results on the central B-scan are presented for the same subject in FIGS. 10A to 10C. As shown in the figures, the method according to the invention is able to capture the exact foveal shape with the lowest RMSE (RMSE=2.5 µm) compared to methods M1 (RMSE=4 µm) and M2 (RMSE=8 µm).

Methods M1 and M2 are both using a Gaussian-based basis function to model the foveal shape. Method M2 [2] uses DoG (difference of Gaussian) as basis function for each radial scan and derives three parameters (slope, rim diameter and rim height) to characterize the shape of the fovea, which is a too small number to encounter all the variation of the fovea shape. The optimization procedure of the mentioned energy function in this method is complex, which makes the energy function having unstable minima quite often. The method M1 [1] applies a Gaussian along with a quadratic and linear basis function to produce a 3D model of a volume scan. It needs eight parameters ($A_0$, $A_{11}$, . . . , $A_{22}$) to reconstruct a 3D model of a volume scan.

However, these parameters do not represent any morphological information of the fovea, which makes their interpretation in relation to the morphological characteristics rather difficult. Scheibe et al. introduced a stable and accurate modeling of the fovea using the double derivative of an exponential function [9]. This method [9] is applied to re-sampled radial scans from 3D macula cube scans. There are four parameters used to parametrize a radial scan. However, the parameter y in the exponential basis function (exp(−x$^y$)) [9] makes the algorithm more complex and leads to difficulties in optimization and analytical analyses. Additionally, the direct analytical derivation of 3D parameters, e.g. volumes presents several computational problems.

Recently, Liu et. al [5] has introduced a sloped piecemeal Gaussian model for characterizing the foveal pit shape. This method uses a combination of linear and Gaussian basis function along with an additional parameter which encounters the pit bottom flatness. As this method is using piecewise basis function, the optimization process is not straight forward. However, this method only characterizes the foveal pit and not the complete fovea shape. In FIG. 11, different RMSE values for 3D fitting on a volume scan are shown as box plot. These RMSE values are computed between raw ILM-RPE segmented data (as mentioned in section 3.2) from Heidelberg Spectralis OCT and the corresponding fitted model. The comparison has been performed between the method according to the invention and methods M1, M2. The RMSE values for our approach show overall lower values compared to other methods as the method according to the invention reconstructs the foveal pit more accurately as shown in FIGS. 10A to 10C. In the method according to the invention, the highest RMSE occurs in regions where the segmentation is mostly influenced by blood vessels. These blood vessels produce several "jumps" spatially close to each other as shown in FIG. 12 (bottom).

These "jumps" have a strong influence also in the detection of maximum height points (rim points), which can lead to a higher RMSE because the parametrization scheme of the invention depends on these critical points. In such cases, peaks are representing vessels and not the retinal tissue, which might induce additional noise when investigating differences between healthy and pathological data [8].

An important aspect of the method according to the invention is its ability to utilize characteristic fovea properties for the whole circular region (re-sampled radial region) because of the flexible and robust cubic Bézier parametrization scheme. This implies that the discussed 3D parameters are derived in a completely new fashion and opens up the possibility to explore new morphological features of the fovea in terms of the Rim Disk, Slope Disk, and Pit Flat Disk by looking at eigenvectors of the covariance matrix defined in Equation 19. By computing the pit flatness and its area from the 3D reconstruction, it is possible to provide not only a better visual insight of this region but also a potentially new diagnostic parameter for further investigation into several diseases e.g. those characterized by nerve fibers and ganglion cells loss [6, 7, 11]. Another beneficial aspect of the presented 3D approach is in the flexibility of defining the foveal radius. This can be computed from the model itself as a specific feature of each radial Bézier curve part, and as such it would take into account the asymmetric nature of this region, or as a variable radius, defined by the user.

5.3 Applications in HC and Patients with Autoimmune Neuroinflammatory Disorders Having all parameters described in the previous section, it is possible to perform a first analysis of morphological aspects of the data set. Table 3 shows all 3D parameters defined for the HC and patient groups. Measurements obtained with the method according to the invention have similar values to the ones encountered in the literature. For characteristics like Rim Disk Area, Slope Disk Area, Pit Flat Disk Area a comparison to the existing literature is not possible since this is the first time that these parameters have been introduced.

Also the capability of the derived parameters to differentiate between HC and non-healthy patients was investigated. To this end GEE analyses were performed. Table 3 represents that several shape parameters show significant differences between HC and patients.

TABLE 3

Analysis of all 3D parameters defined for HC, and patient groups. The last column shows results of the GEE analysis between the two groups. Abbreviations: HC - healthy control group; SD - standard deviation; Min - Minimum value; Max - maximum value; GEE - generalized estimating equation models analysis accounting for inter-eye/intra-subject dependencies; p - p-value.

| | HC | | Patients | | GEE |
|---|---|---|---|---|---|
| Parameters | Mean (SD) | Min-Max | Mean (SD) | Min-Max | p |
| Avg. Pit Depth ($h_p$) (mm) | 0.128 (0.019) | 0.079-0.165 | 0.110 (0.022) | 0.040-0.150 | 9.48E−05 |
| Central Foveal Thickness ($h_{cft}$) (mm) | 0.224 (0.016) | 0.186-0.266 | 0.223 (0.014) | 0.199-0.264 | 0.628 |
| Avg. Rim Height ($h_r$) (mm) | 0.352 (0.014) | 0.319-0.389 | 0.335 (0.018) | 0.285-0.378 | 5.73E−08 |
| Avg. Rim Disk Diameter ($d_r$) (mm) | 2.130 (0.190) | 1.680-2.580 | 2.140 (0.170) | 1.760-2.510 | 0.608 |
| Rim Disk Area ($A_r$) (mm$^2$) | 3.580 (0.660) | 2.220-5.240 | 3.510 (0.590) | 2.440-4.900 | 0.570 |
| Major Axis Rim Disk ($\lambda_3^r$) (mm) | 0.625 (0.110) | 0.372-0.867 | 0.615 (0.100) | 0.420-0.860 | 0.635 |
| Minor Axis Rim Disk ($\lambda_2^r$) (mm) | 0.535 (0.100) | 0.320-0.817 | 0.524 (0.089) | 0.339-0380 | 0.576 |
| Avg. Slope Disk Diameter ($d_s$) (mm) | 0.608 (0.015) | 0.340-0.955 | 0.636 (0.160) | 0.274-1.010 | 0.358 |
| Slope Disk Area ($A_s$) (mm$^2$) | 0.313 (0.120) | 0.100-0.710 | 0.348 (0.170) | 0.059-0.839 | 0.270 |
| Mater Axis Slope Disk ($\lambda_3^s$) (mm) | 0.053 (0.020) | 0.019-0.123 | 0.060 (0.029) | 0.010-0.839 | 0.080 |
| Minor Axis Slope Disk ($\lambda_2^s$) (mm) | 0.045(0.018) | 1.00E−04-0.100 | 0.049(0.026) | 2.00E−05-0.127 | 0.180 |
| Avg. Pit Flat Disk Diameter ($d_f$) (mm) | 0.182(0.031) | 0.110-0.295 | 0.197(0.044) | 0.100-0.433 | 0.083 |
| Pit Flat Disk Area ($A_f$) (mm$^2$) | 0.027(0.010) | 0.011-0.068 | 0.033(0.018) | 0.007-07149 | 0.061 |
| Major Axis Pit Flat Disk ($\lambda_3^f$) (mm$^2$) | 0.004(0.001) | 0.002-0.011 | 0.005(0.003) | 0.001-0.025 | 0.053 |
| Minor Axis Pit Hat Disk ($\lambda_2^f$) (mm$^2$) | 0.004(0.001) | 0.001-0.010 | 0.004(0.002) | 0.001-0.022 | 0.069 |
| Rim Volume ($V_r$) (mm$^3$) | 1.020(0.190) | 0.558-1.544 | 0.944(0.170) | 0.597-1.364 | 0.023 |
| Pit Volume ($V_p$) (mm$^3$) | 0.239(0.44) | 0.152-0.366 | 0.236(0.054) | 0.134-0.384 | 0.766 |
| Inner Rim Volume ($V_{IR}$) (mm$^3$) | 0.110(0.018) | 0.060-0.153 | 0.100(0.019) | 0.062-0.147 | 0.019 |
| Avg. Max. Pit Slope ($s_m$) (Degree) | 12.740(2.680) | 6.320-20.650 | 10.650(2.620) | 3.400-16.290 | 1.38E−05 |
| $\alpha_m$ (mm) | 0.250(0.063) | 0.133-0.470 | 0.250(0.077) | 0.100-0.450 | 0.590 |
| $\beta_m$ (mm) | 0.610(0.1) | 0.360-0.830 | 0.560(0.089) | 0.335-0.845 | 0.005 |

Further features and advantages of the invention shall be described by means of a supplementary figure description, wherein features disclosed in the FIGURE section can also be used in combination with the claimed subject matter. It is shown in FIG. 1 a visualization of a three-dimensional volume data set of retinal structures of interest, comprising the fovea, with highlighted layers ILM (inner limiting membrane), GCL (Ganglion cell layer) and RPE (Retinal pigment epithelium layer);

FIG. 2 B-scans through various foveal pits;

FIG. 3A the central B-scan of a volume with invariant tangent at the critical points;

FIG. 3B the interior and the exterior segment of the right half of the corresponding B-scan. The inner ($P_1$, $P_2$) and end ($P_0$, $P_3$) control points are represented as dots;

FIG. 4 the pipeline (a flow chart) of one embodiment according to the invention;

FIG. 5A a 3D shape reconstruction procedure of the fovea. A volume scan with 61 B-scans and 768 A-scans and corresponding 24 radial directions, representing the radial height profiles (white lines) using a bilinear interpolation.

FIG. 5B the 24 fitted model-functions (black line) fitted to the radial height profiles (white lines) using a least square optimization. The black circular rings show the second end point of the first Bézier function as well as the first end point from the second Bézier function for each radial scan (the black circular rings are also referred to as critical points);

FIG. 6A a 2D shape reconstruction, wherein re-sampled radial scans from a volume scan divided in two parts $c(r, \theta_i)$ and $c(r, \theta_i+\pi)$ are shown;

FIG. 6B corresponding fitted radial scans using the least square optimization which are represented by is $Q(t, \theta_i)$ and $Q(t, \theta_i+\pi)$ and i=1, . . . ,n. A full radial scan can be considered as a combination of $c(r, \theta_i)$ and $c(r, \theta_i+\pi)$;

FIG. 7 a visualization of the 2D parameters on the central B-scan:

FIG. 8A a top view of the rim disk;

FIG. 8B a normal vector of the rim disk plane and corresponding covariance eigenvalues and eigenvectors;

FIG. 9A to FIG. 9D a visual representation of the 3D parameters. The rim and the inner rim volume is defined as the volume covered by the corresponding disk area. The radius for the inner disk area and the volume is defined by user;

FIG. 9A a rim disk, particularly the rim disk area;

FIG. 9B an inner rim disk—all points are at 0.5 mm form the foveal center used for the inner rim volume computations;

FIG. 9C a slope disk, particularly the slope disk areas;

FIG. 9D a pit disk, particularly the pit disk area;

FIG. 10A to FIG. 10C a comparison of the method according to the invention with two state-of-the-art methods [1] and [2]. The dotted line is the raw input (ILM-RPE difference), particularly the height profile at the central B-scan and the solid black or grey lines represent the reconstructed curves with [2], [1] and the method according to the invention (CuBe), respectively.

FIG. 11 RMSE values for 3D M1, M2, and CuBe for the whole data set.

FIG. 12 two examples of the 2D curve fitting results with the lowest (top) and the highest (bottom) RMSE values selected from the entire data set analyzed. The original data is shown as dotted line and the fitted curve is given as dashed line. The RMSE values are from top to bottom, 1.0 µm, 7.1 µm.

FIGS. 13 to 31 the results for various shape parameters estimated with the method according to the invention are shown for a cohort of human patients, wherein the demographic data of said cohort is shown in the following table 4.

FIG. 32 depicts Table 5, a performance of the classification of patients of the MS and HS group.

FIG. 33 depicts Table 6, a performance of the classification of patients of the HS group only.

FIG. 34 depicts Table 6, a performance of the classification of patients of the MS group only.

6. CLINICAL RESULTS

Figure 1:
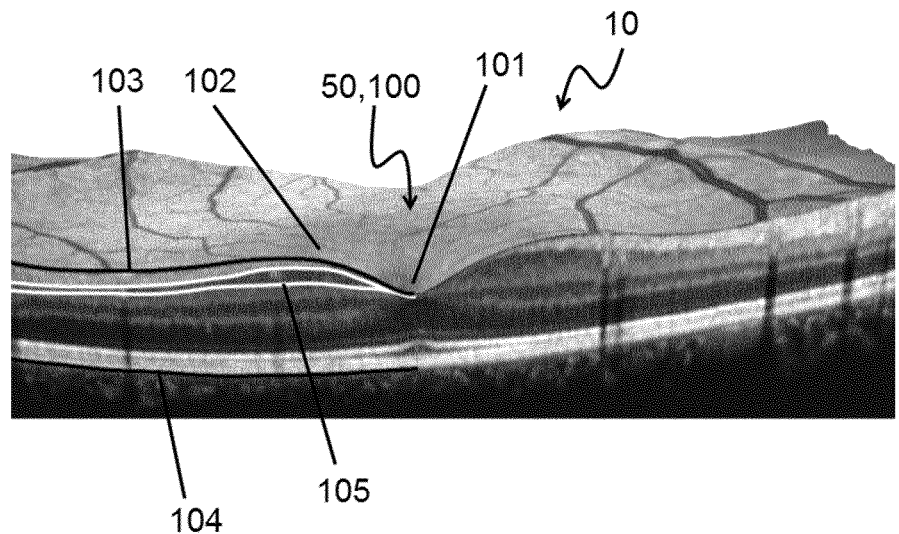
Figure 2:
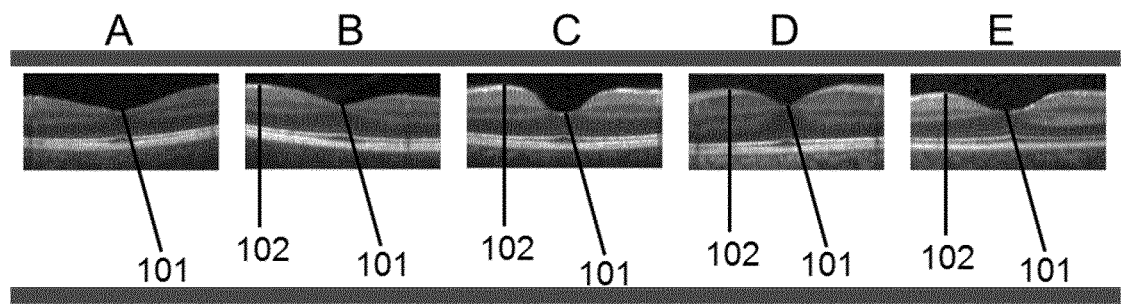
Figure 3A:
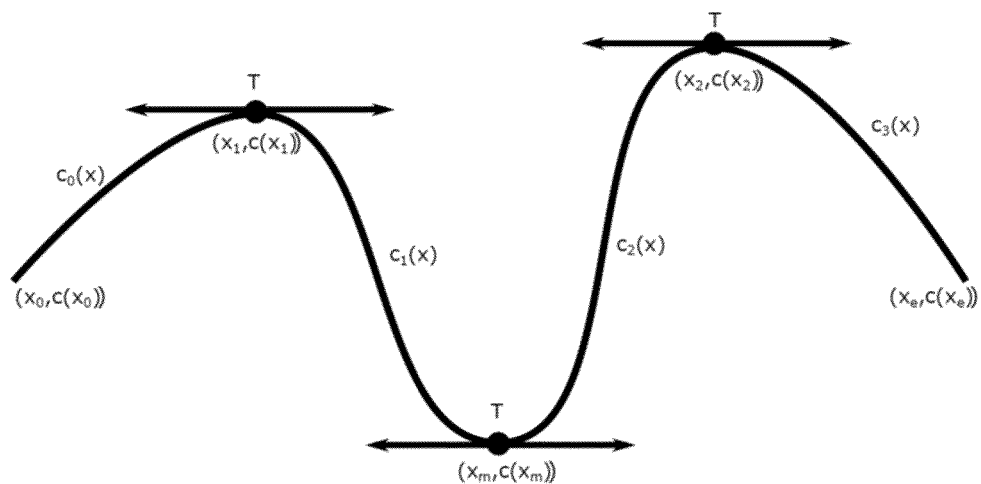
Figure 3B:
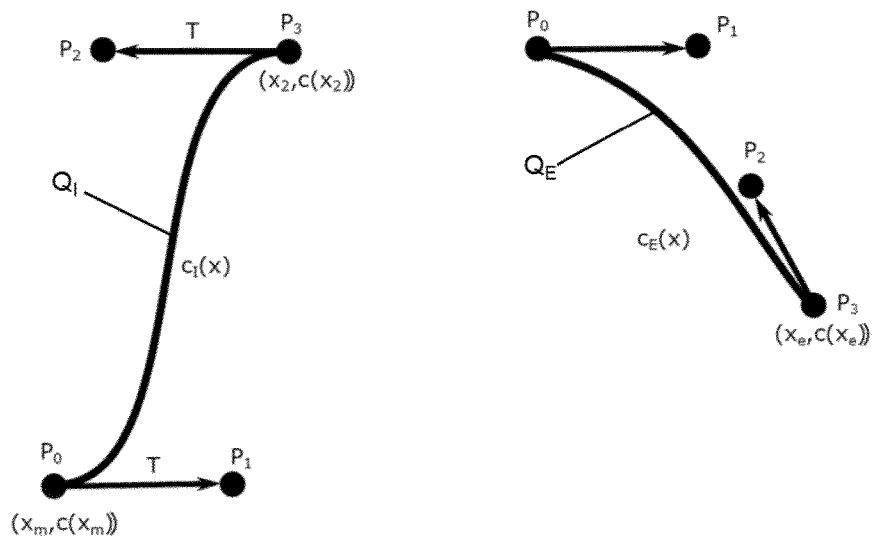
Figure 4:
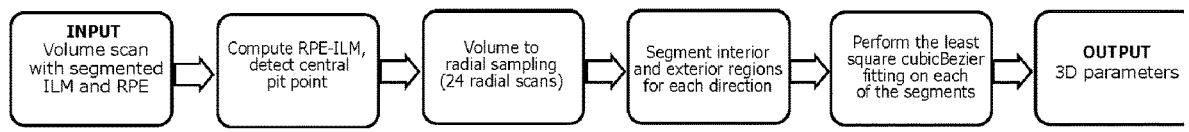
Figure 5A:
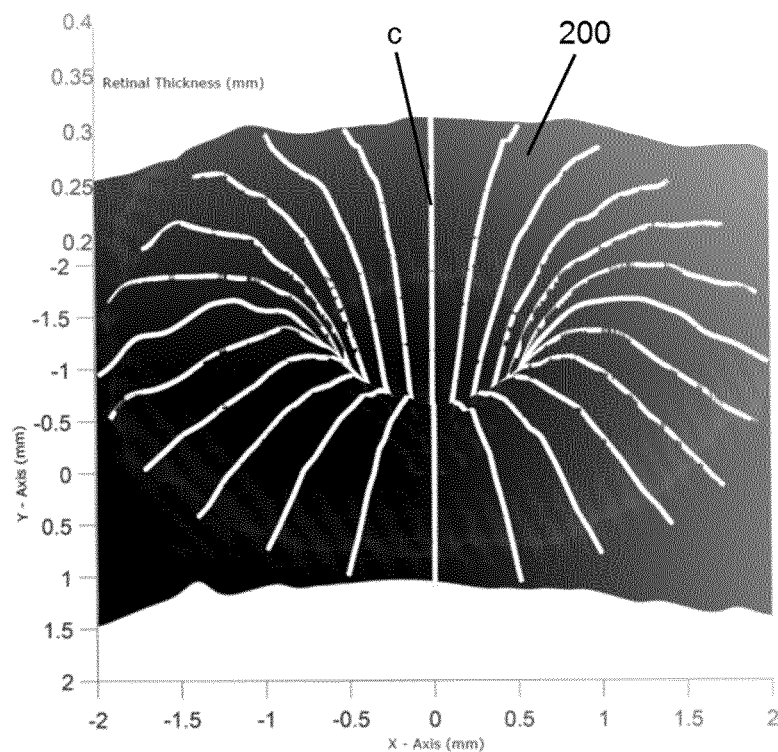
Figure 5B:
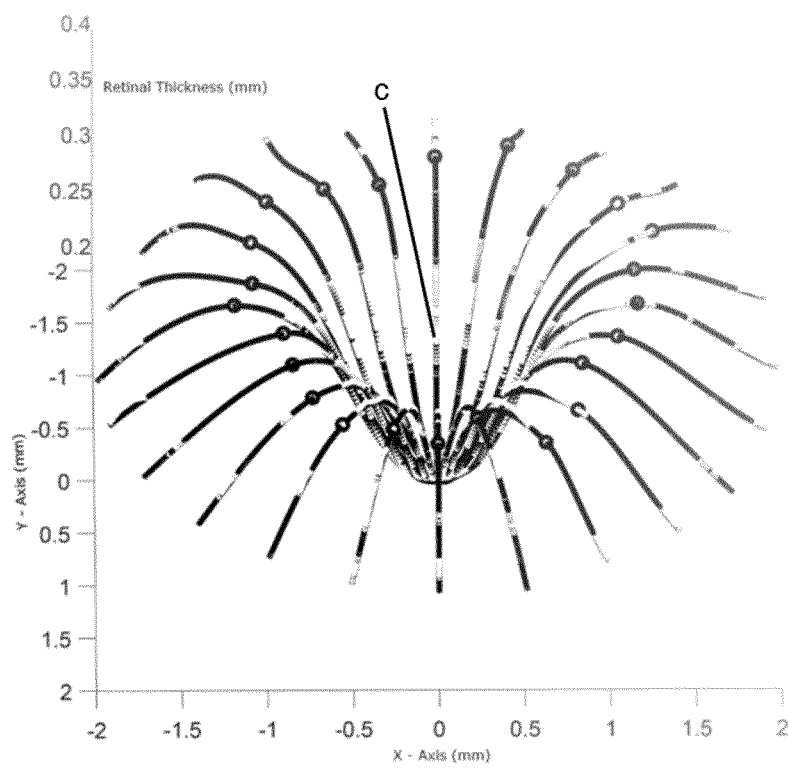
Figure 6A:
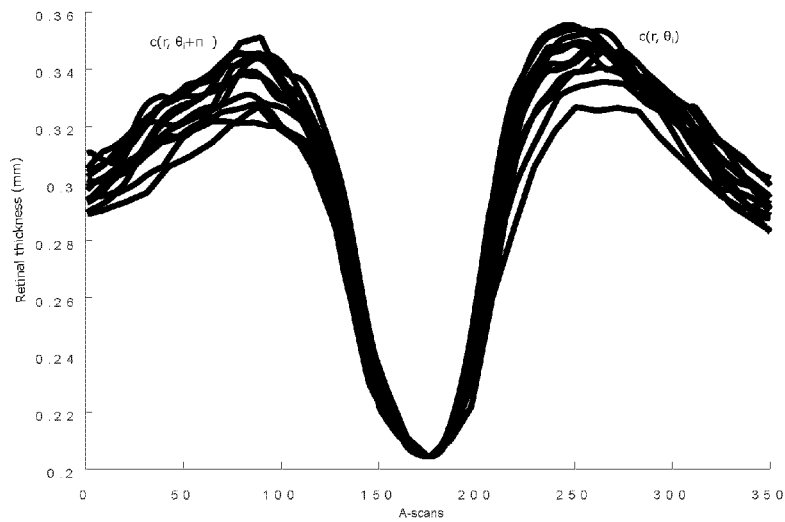
Figure 6B:
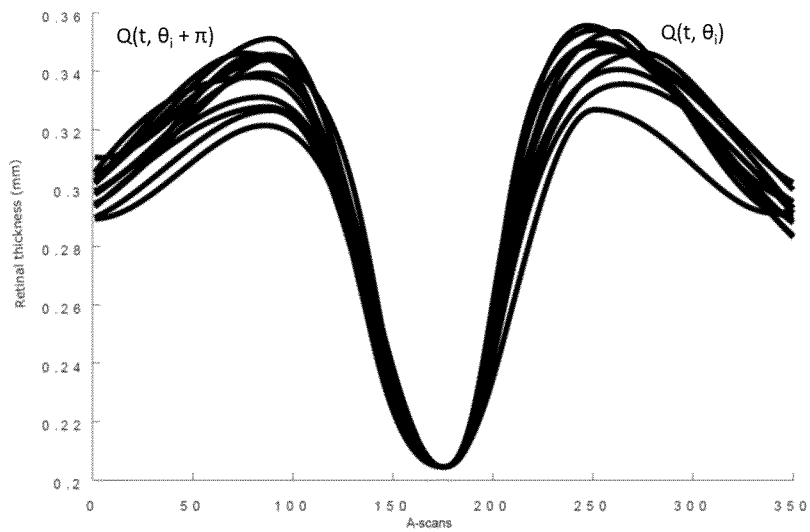
Figure 7:
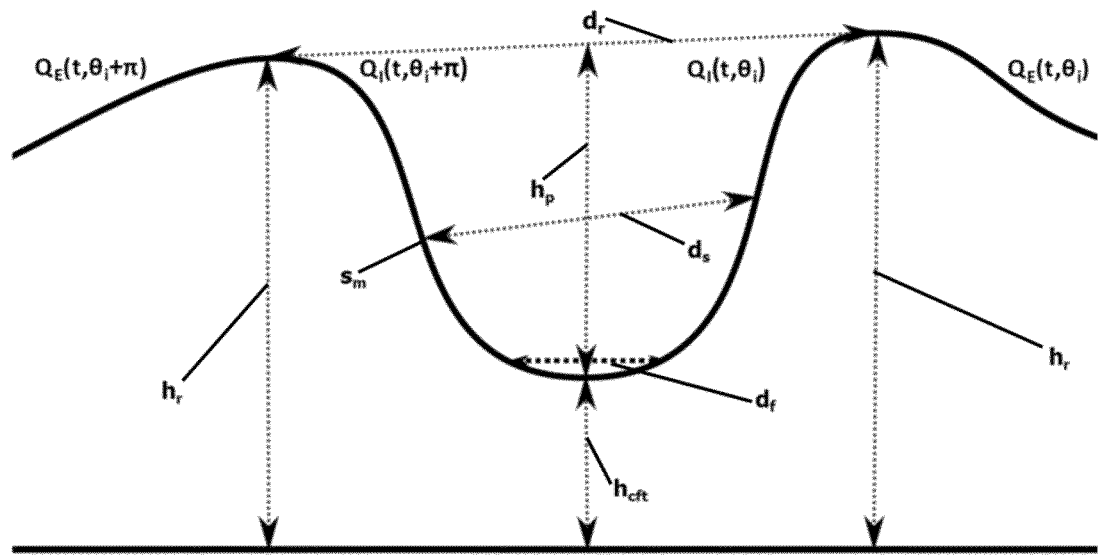
Figure 8A:
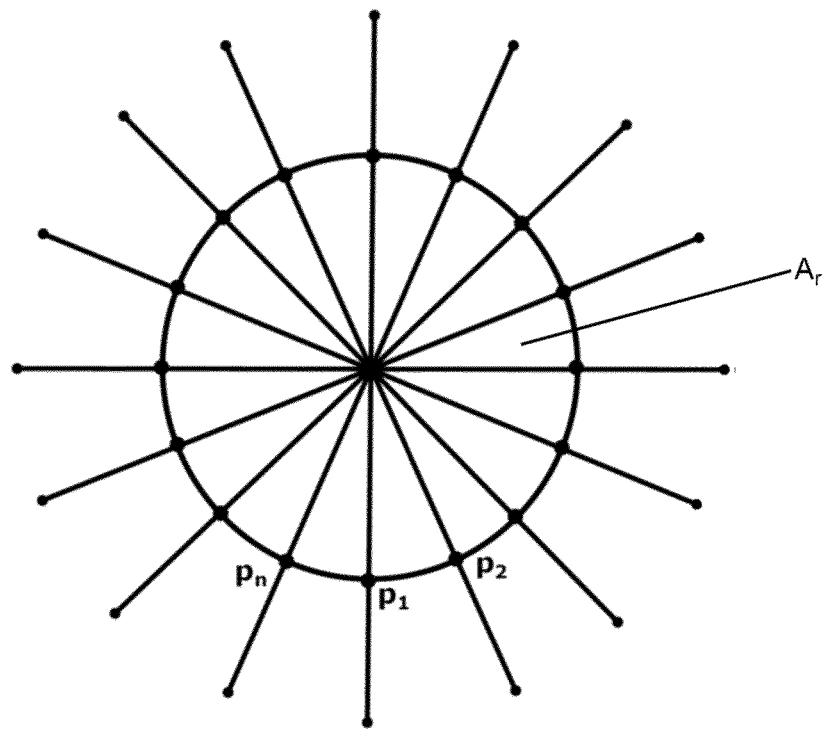
Figure 8B:
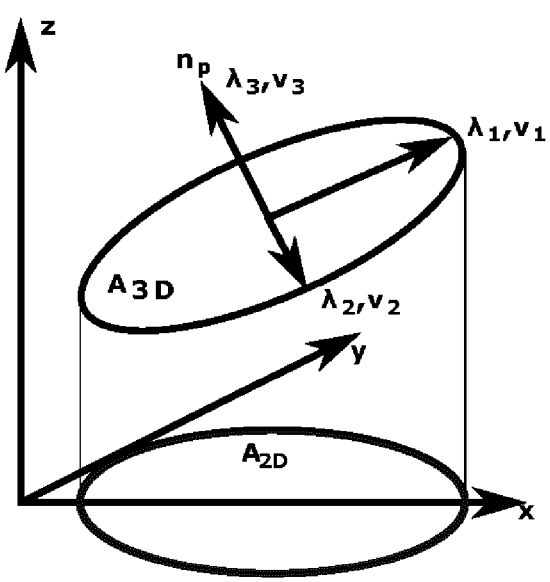
Figure 9:
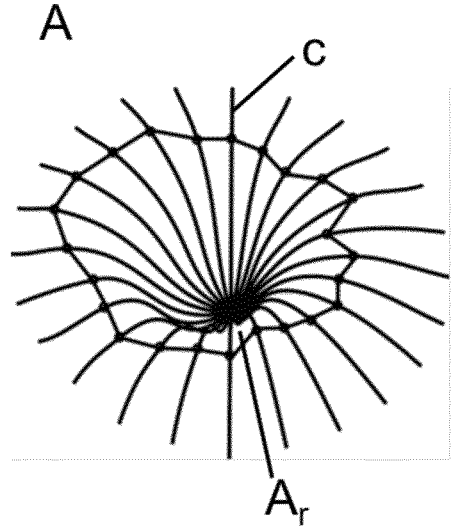
Figure 9:
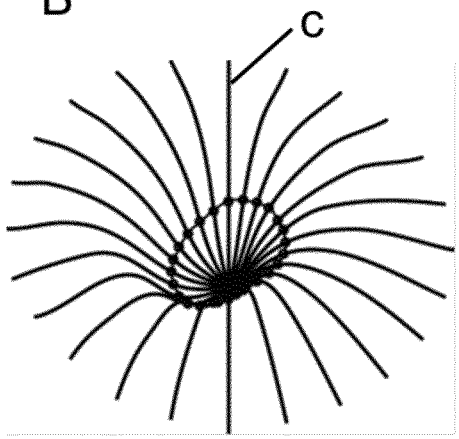
Figure 9:
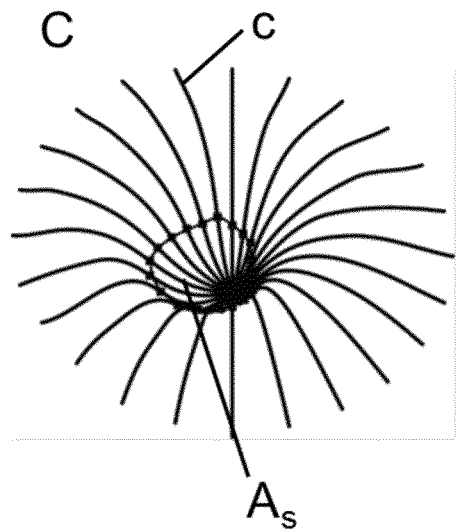
Figure 9:
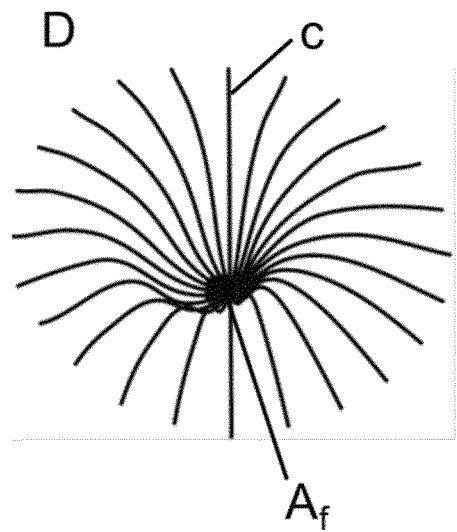
Figure 10A:
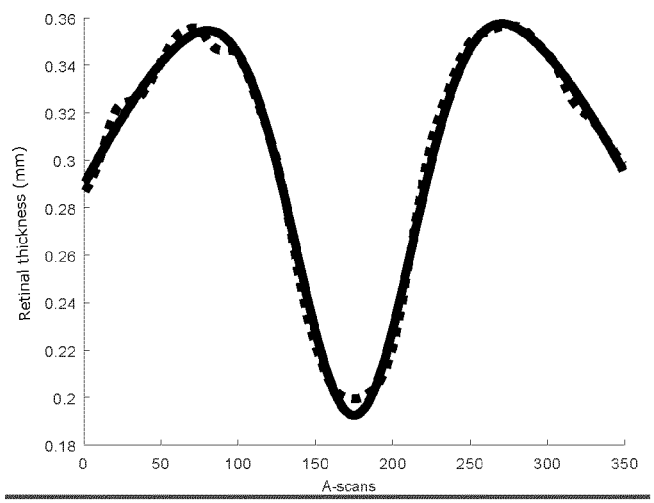
Figure 10B:
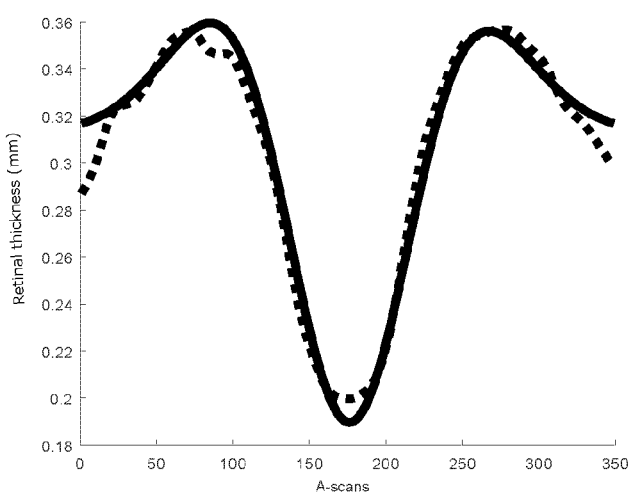
Figure 10C:
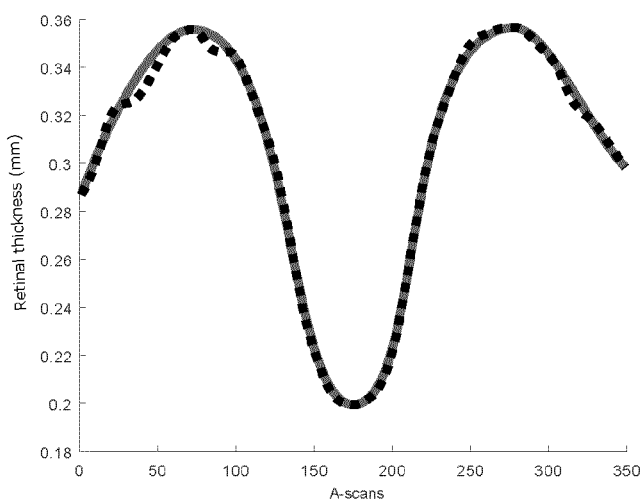
Figure 11:
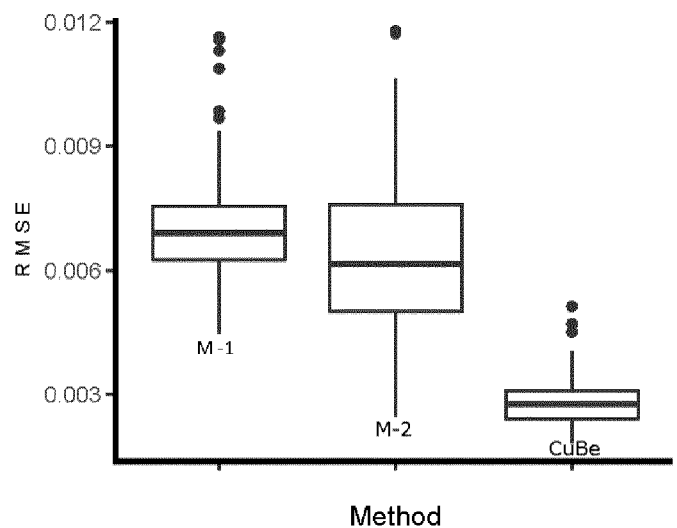
Figure 12:
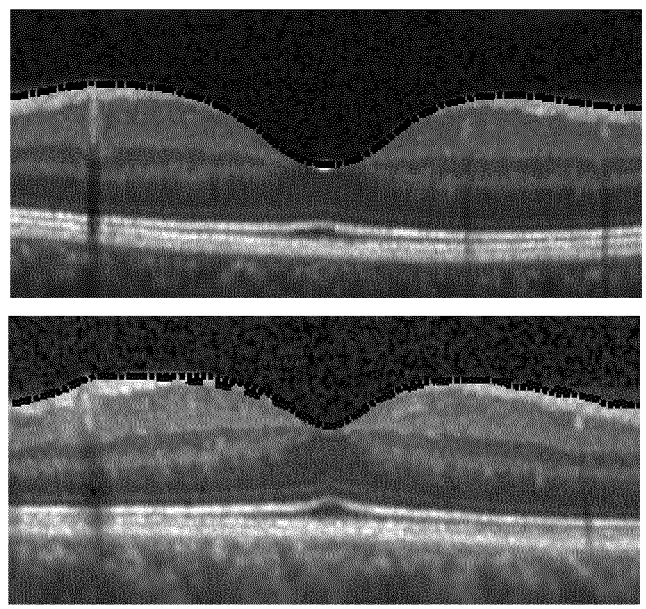

In FIGS. 13 to 31 the results for various shape parameters estimated with the method according to the invention are shown for a cohort of human patients, wherein the demographic data of said cohort is shown in the following table 4.

TABLE 4

|  | HC | MS | NMOSD AQP4-ab pos. | NMOSD MOG-ab pos. | NMOSD ab-neg. |
|---|---|---|---|---|---|
| Number of patients [n] | 28 | 64 | 28 | 11 | 3 |
| Number of eyes [n] | 56 | 122 | 52 | 19 | 5 |
| sex *[female/male] | 25/3 | 58/6 | 26/2 | 8/3 | 2/1 |
| age **[years, mean ± SD] | 38.06 ± 16.23 | 39.69 ± 11.28 | 43.55 ± 11.5 | 39.36 ± 13.76 | 42.26 ± 15.85 |
| Patients with history of ON [n] | — | 31 | 16 | 9 | 3 |
| Eyes with history of ON [n] | — | 35 | 20 | 13 | 5 |
| Number of ONs per eye [median; range] | — | 1 [1.3] | 1 [0.3] | 2 [1.8] | 1 [0.8] |

* Sex matching: p-value = 1
** Age matching p-value: HC vs MS = 0.9, HC vs NMO = 0.1, and NMO vs MS = 0.05!

In FIGS. 13 to 31 the results from the cohort of table 4 for various shape parameters are shown.

In the FIGS. 13-31, each first column is related to the respective shape parameter estimated for the healthy control group (HC). The respective estimated parameter is presented as a box plot wherein the boxed region corresponds to the first and third quantiles and the horizontal line inside the boxed region corresponds to the second quantile (median). The vertical lines extending from each side of the boxed region to the last point less than 1.5 times the length of the box away. Each mark corresponds to a measurement. A mark is a circle or a triangle wherein a circle represents data from a female (f) patient and a triangle represents data form a male (m) patient. The age (in years) of the patient is indicated by the particular grey level.

The text "NON" at the x-axis refers to a group that did not suffer from an optical neuritis. The text "ON" at the x-axis refers to a group that did suffer from an optical neuritis.

Analogous to the HC column, the following columns are shown:
- a "MS" column, differentiating between patients having suffered from ON ("ON") and patients that have not suffered ON ("NON"), that shows the results of the respective estimated parameter for a group diagnosed with MS;
- a "NMO_AQP4ab+" column, differentiating between patients having suffered from ON ("ON") and patients that have not suffered ON ("NON"), that shows the results of the respective estimated parameter for a group diagnosed with NMO, wherein this group was tested positive for Aquaporin-4 antibodies;
- a "NMO MOGab+" column, differentiating between patients having suffered from ON ("ON") and patients that have not suffered ON ("NON"), that shows the results of the respective estimated parameter for a group diagnosed with NMO-like disease (MOG-ab encephalomyelitis), wherein this group was tested positive for MOG antibodies but negative for Aquaporin-4;

a "NMOab−" column, with patients having suffered from ON ("ON"), that shows the results of the respective estimated parameter for a group diagnosed with NMO, wherein this group was tested negative for Aquaporin-4 antibodies;

Furthermore, each Figure comprises a table listing some statistical analysis of the respective estimated shape parameter, such as the mean value ("Mean"), the standard deviation ("STD"), the largest value ("MAX") and the smallest value ("MIN") of the parameter.

Figure 13:
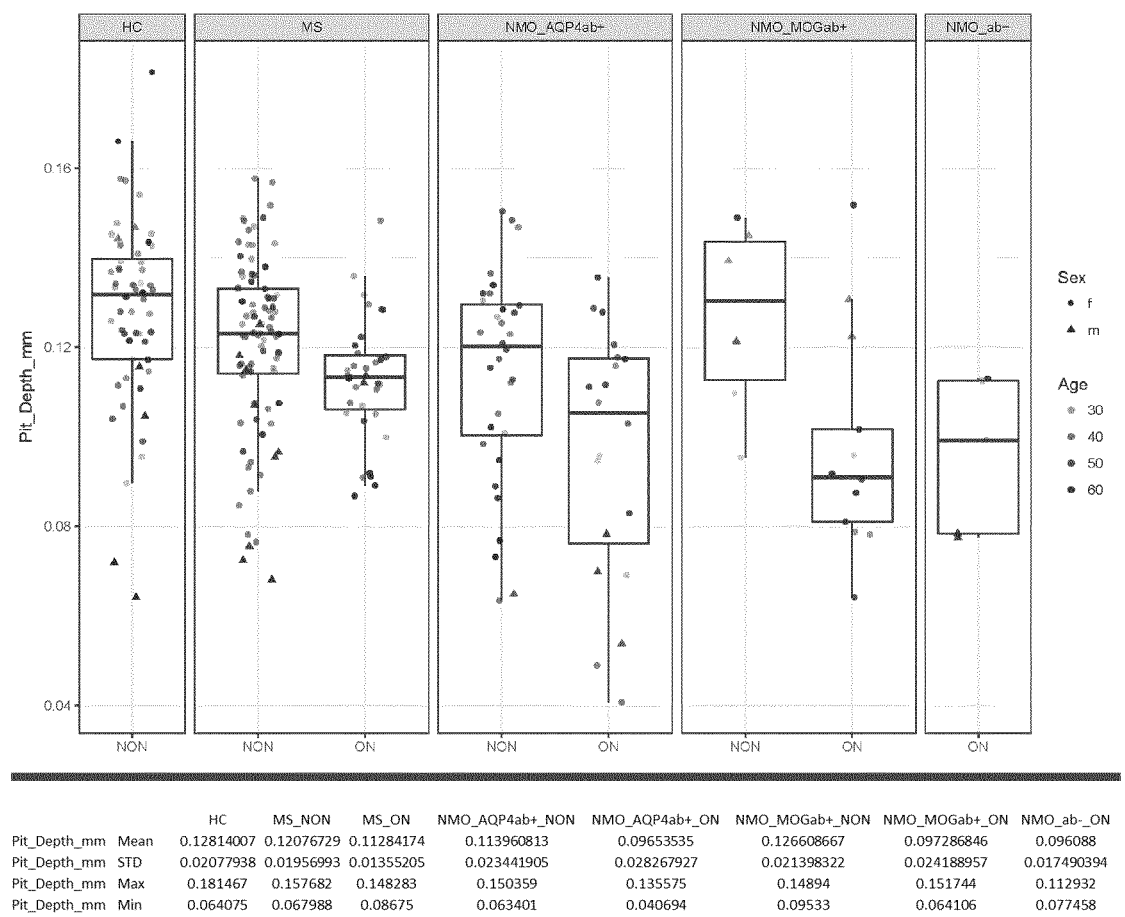

In FIG. 13 the results from the cohort of table 4 for the shape parameter 'average pit depth' $h_p$ ("pit depth") are shown. The average pit depth $h_p$ is measured in mm.

Figure 14:
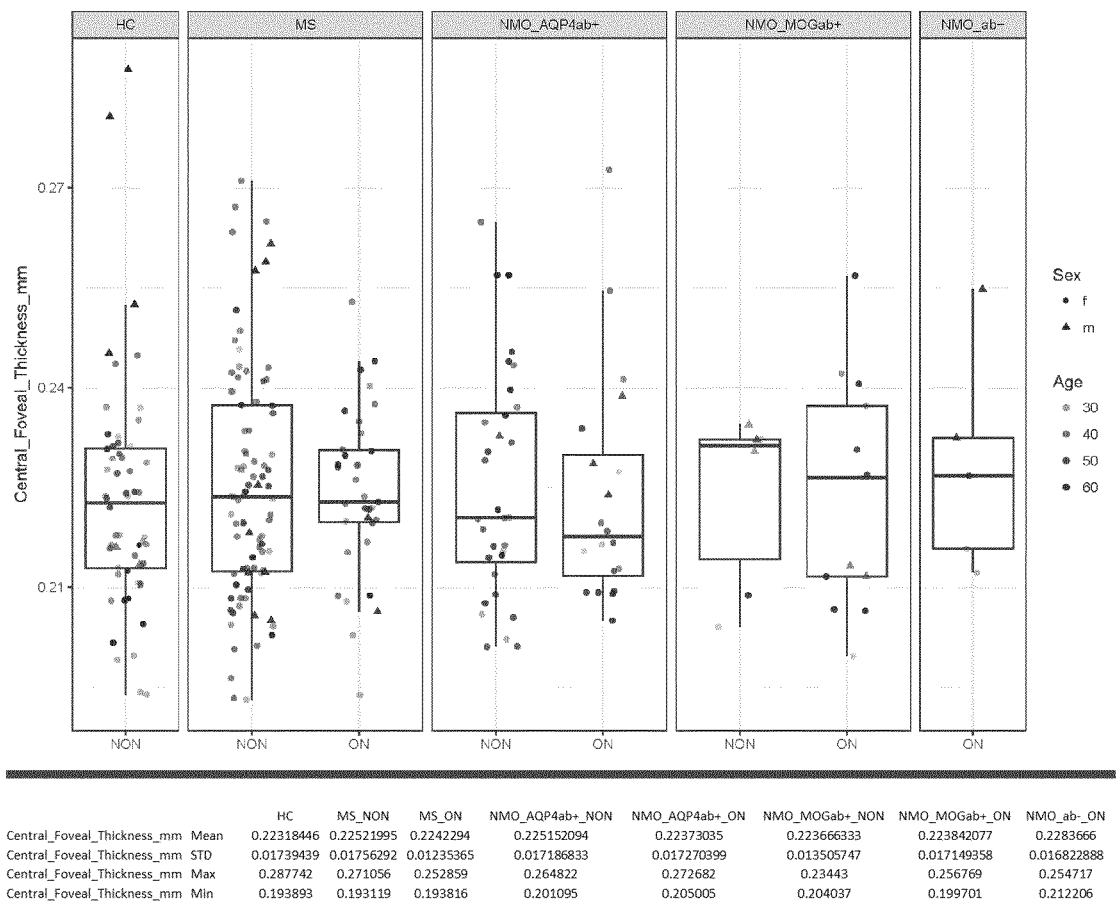

In FIG. 14 the results from the cohort of table 4 for the shape parameter 'central foveal thickness' $h_{cft}$ are shown. The central foveal thickness $h_{cft}$ is measured in mm.

Figure 15:
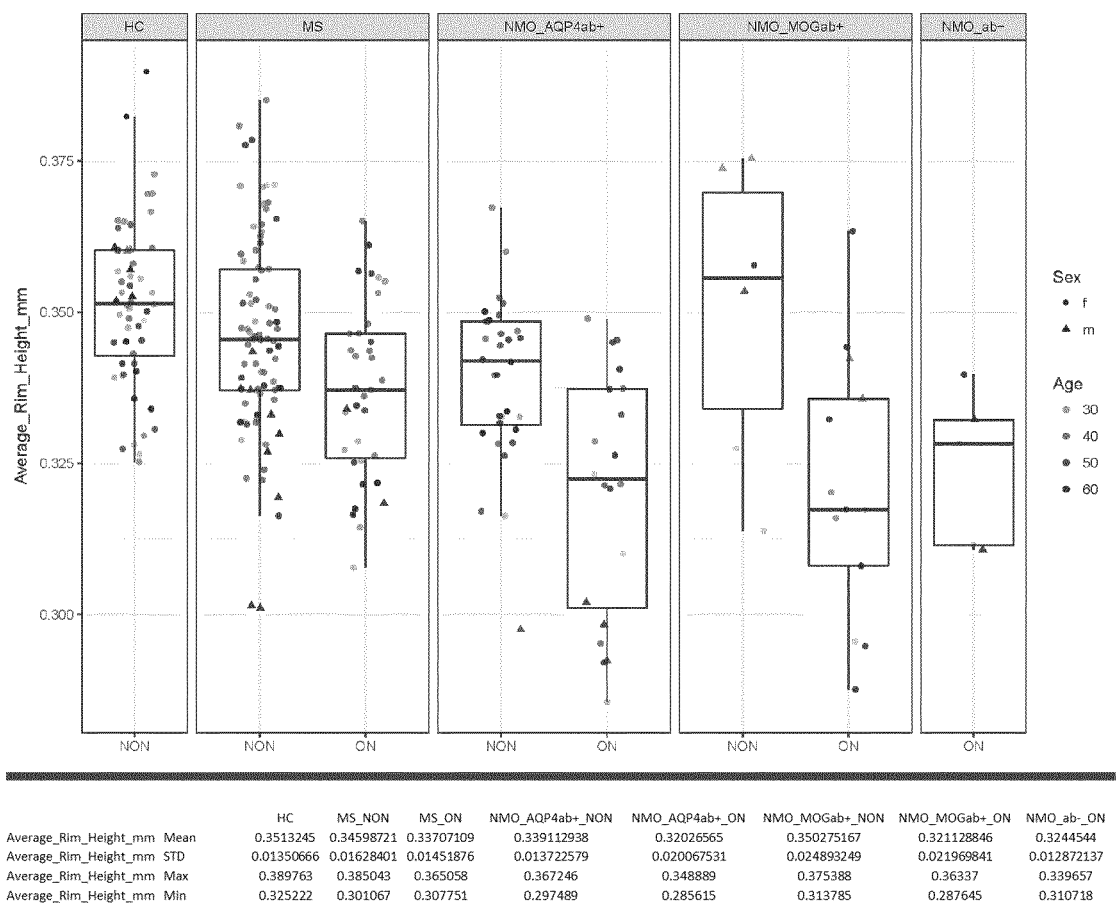

In FIG. 15 the results from the cohort of table 4 for the shape parameter 'average rim height' $h_p$ are shown. The average rim height $h_p$ is measured in mm.

Figure 16:
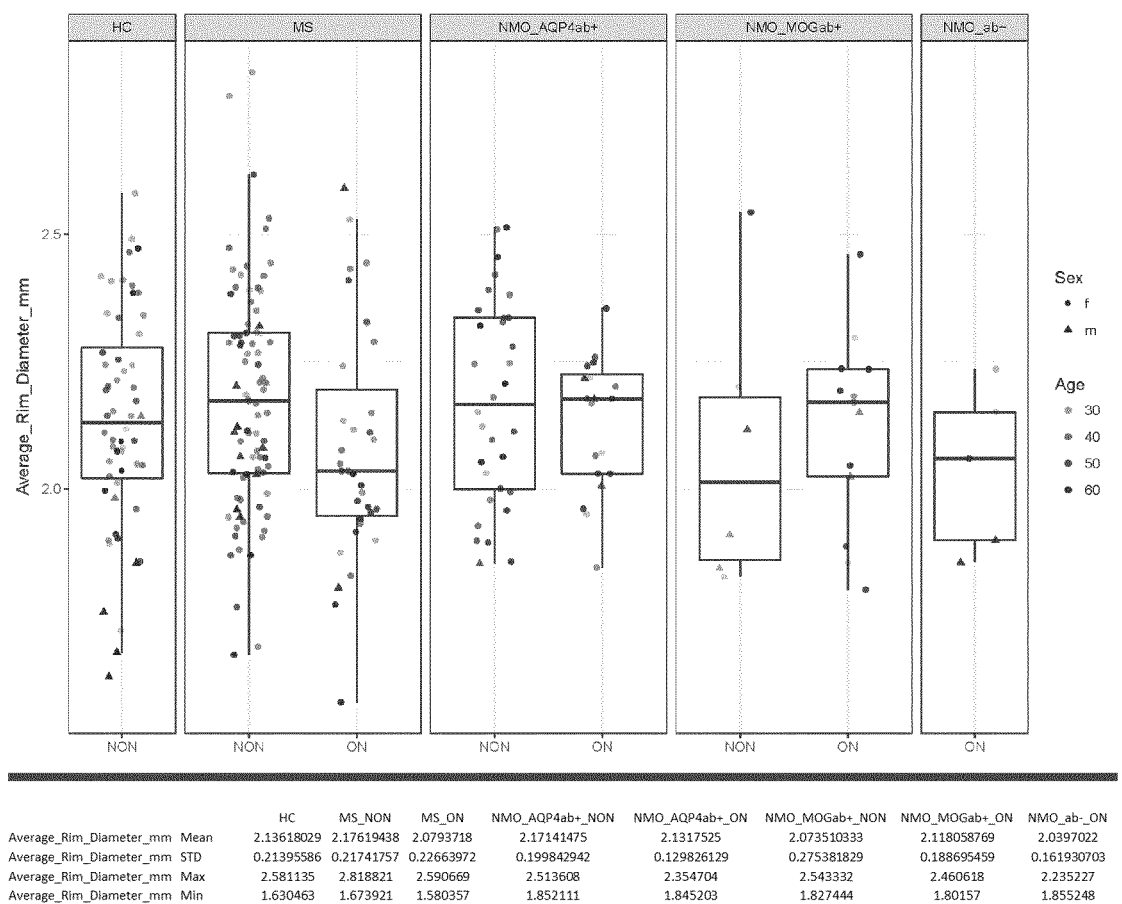

In FIG. 16 the results from the cohort of table 4 for the shape parameter 'average rim disk diameter' $d_r$ ("average rim diameter") are shown. The average rim disk diameter $d_r$ is measured in mm.

Figure 17:
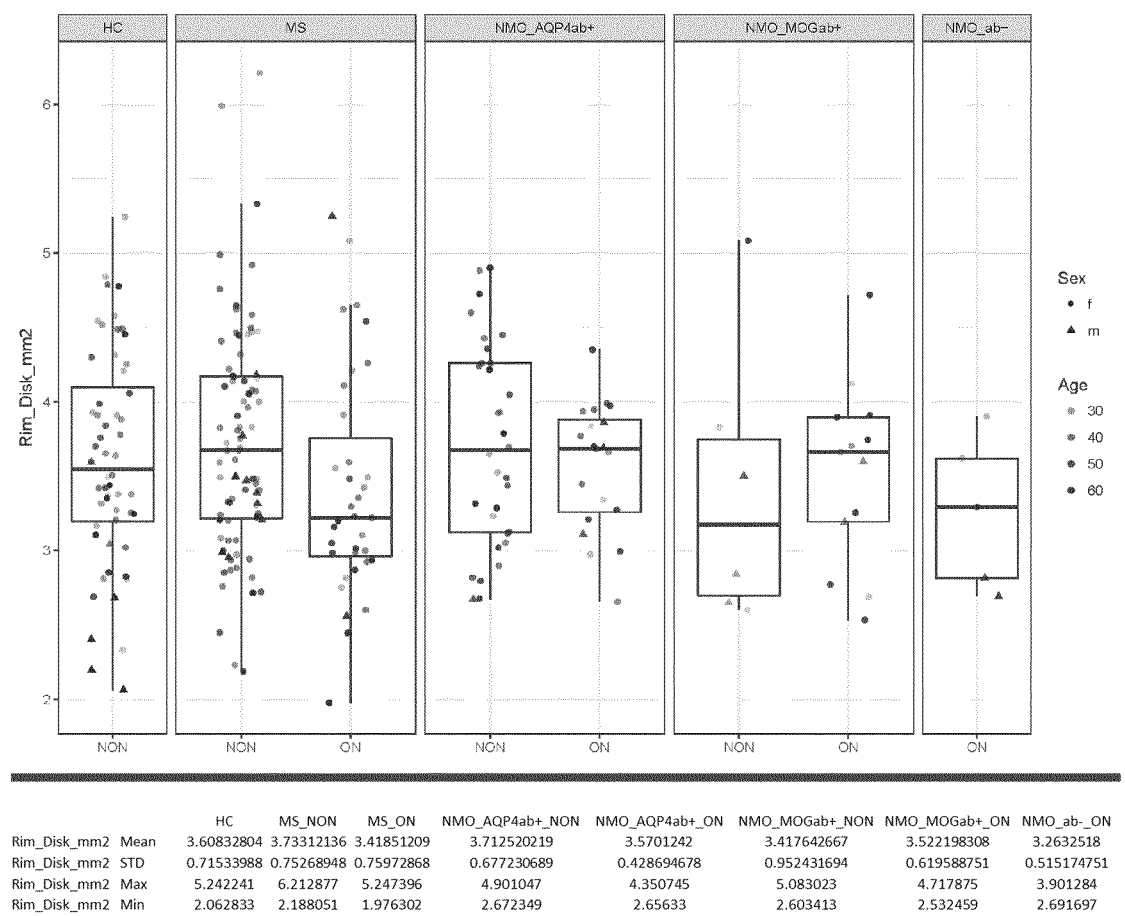

In FIG. 17 the results from the cohort of table 4 for the shape parameter 'rim disk area' $A_r$ ("rim disk") are shown. The rim disk area $A_r$ is measured in $mm^2$.

Figure 18:
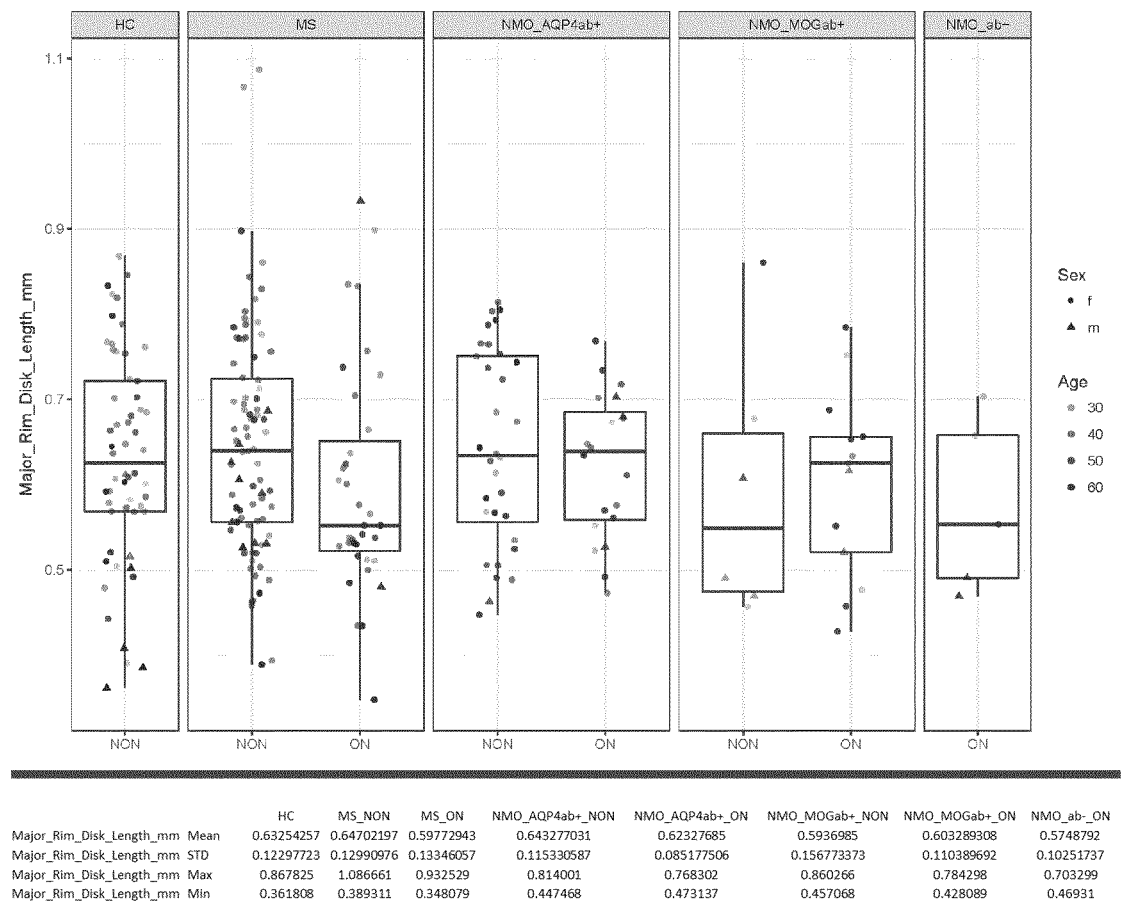

In FIG. 18 the results from the cohort of table 4 for the shape parameter 'major axis length of the rim area' $\lambda_3^r$ ("major rim disk length") are shown. The major axis length $\lambda_3^r$ is measured in mm.

Figure 19:
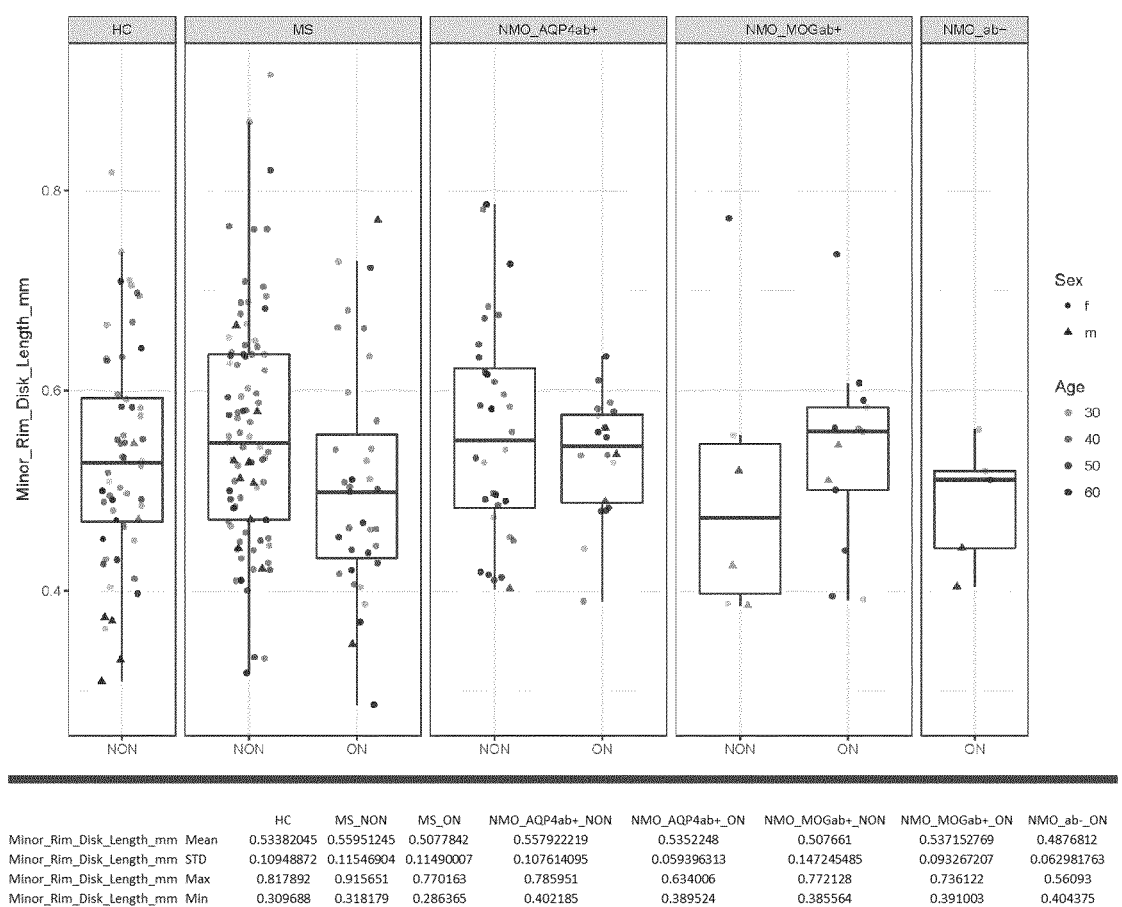

In FIG. 19 the results from the cohort of table 4 for the shape parameter 'minor axis length of the rim area' $\lambda_2^r$ ("minor rim disk length") are shown. The minor axis length $\lambda_2^r$ is measured in mm.

Figure 20:
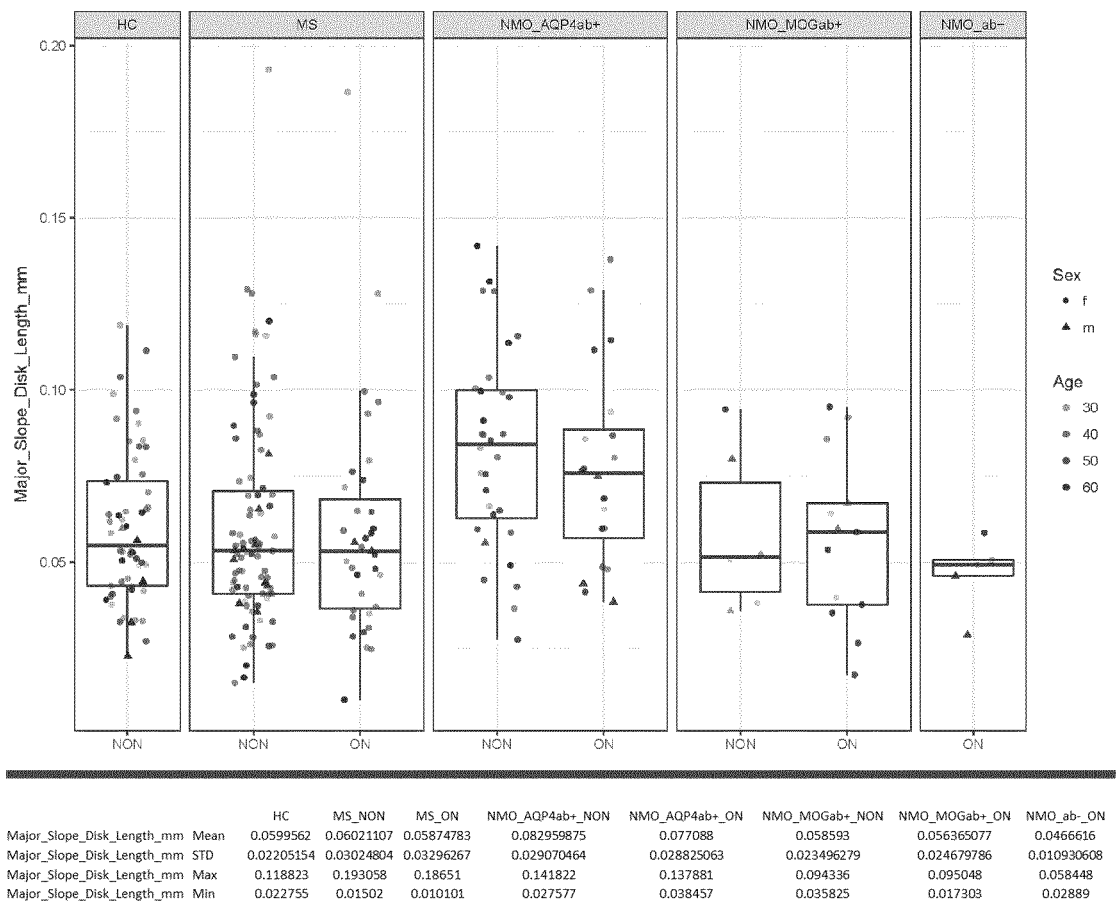

In FIG. 20 the results from the cohort of table 4 for the shape parameter 'major axis length of the slope disk area' $\lambda_3^s$ ("major slope disk length") are shown. The major axis length $\lambda_3^s$ is measured in mm.

Figure 21:
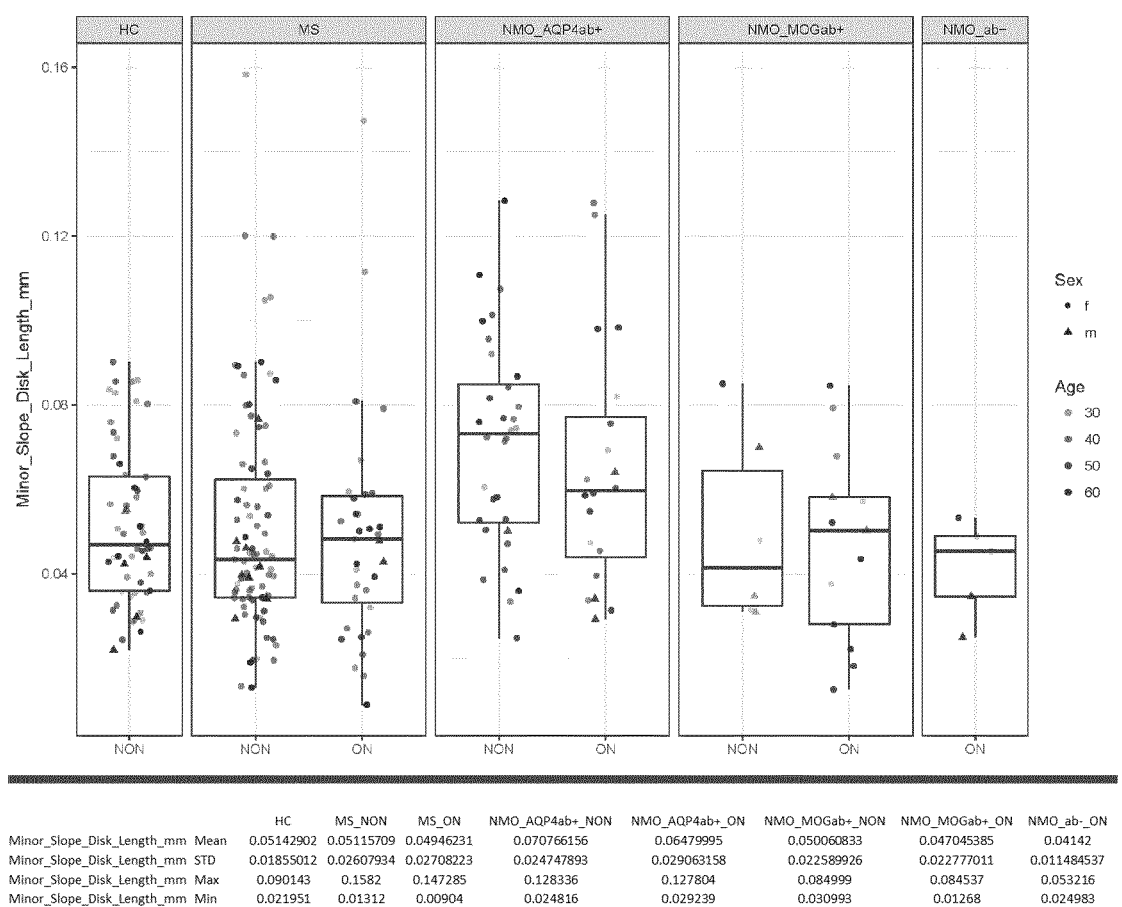

In FIG. 21 the results from the cohort of table 4 for the shape parameter 'minor axis length of the slope disk area' $\lambda_2^s$ ("minor slope disk length") are shown. The minor axis length $\lambda_2^s$ is measured in mm.

Figure 22:
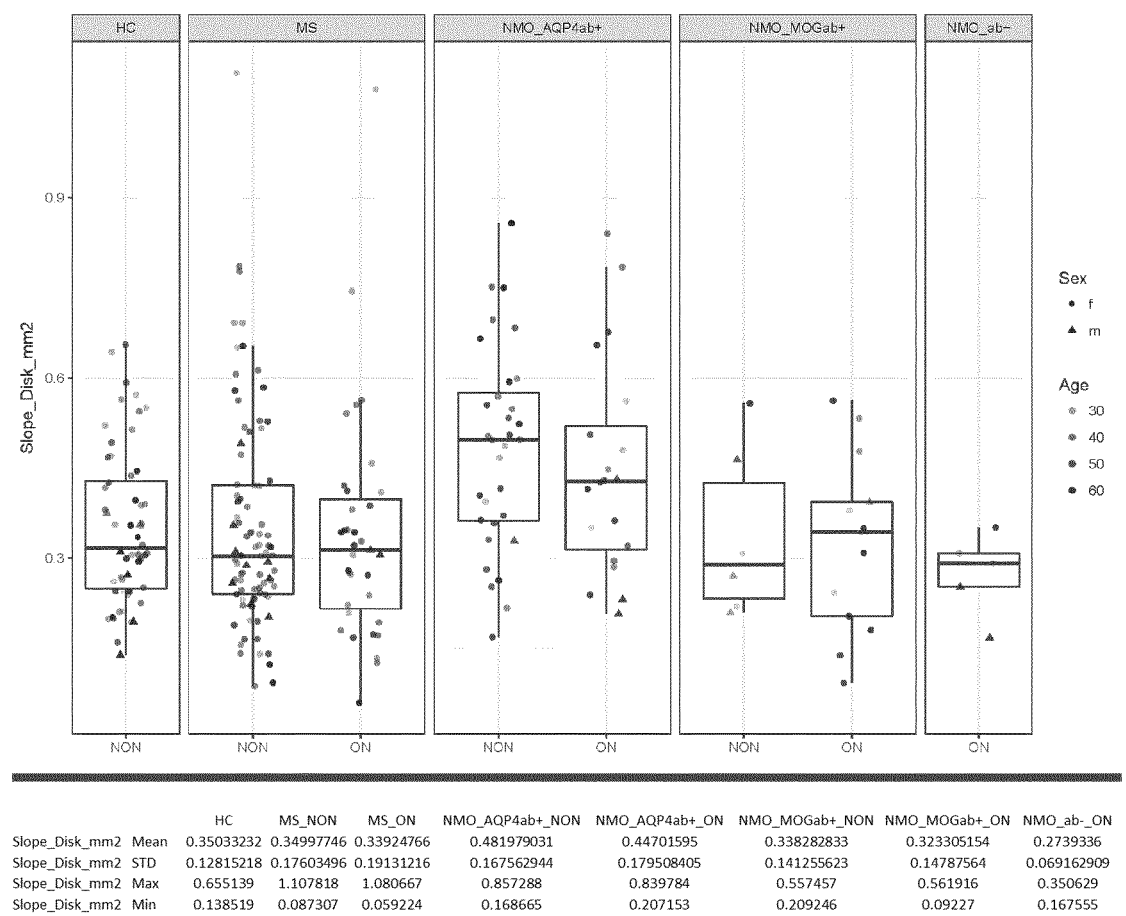

In FIG. 22 the results from the cohort of table 4 for the shape parameter 'slope disk area' $A_s$ ("slope disk") are shown. The slope disk area $A_s$ is measured in $mm^2$.

Figure 23:
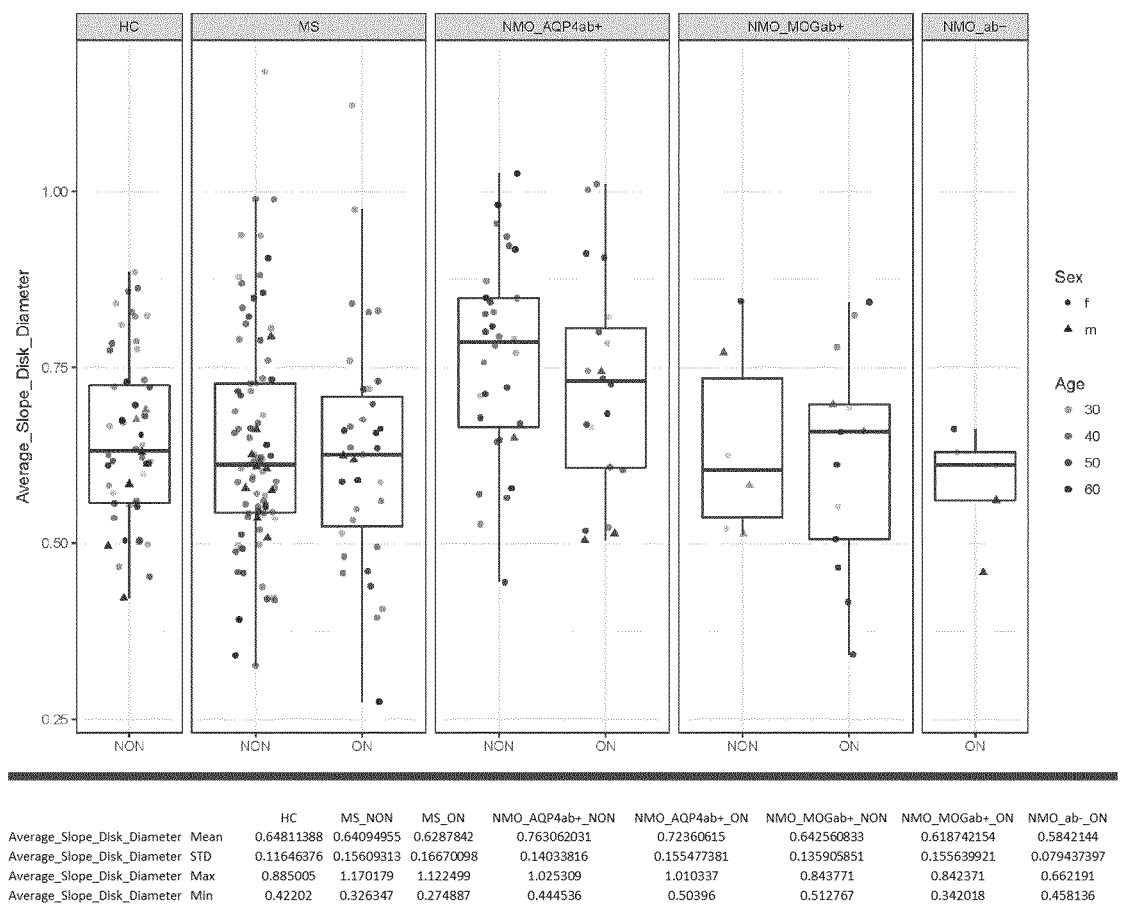

In FIG. 23 the results from the cohort of table 4 for the shape parameter 'average slope disk diameter' $d_s$ are shown. The average slope disk diameter $d_s$ is measured in mm.

Figure 24:
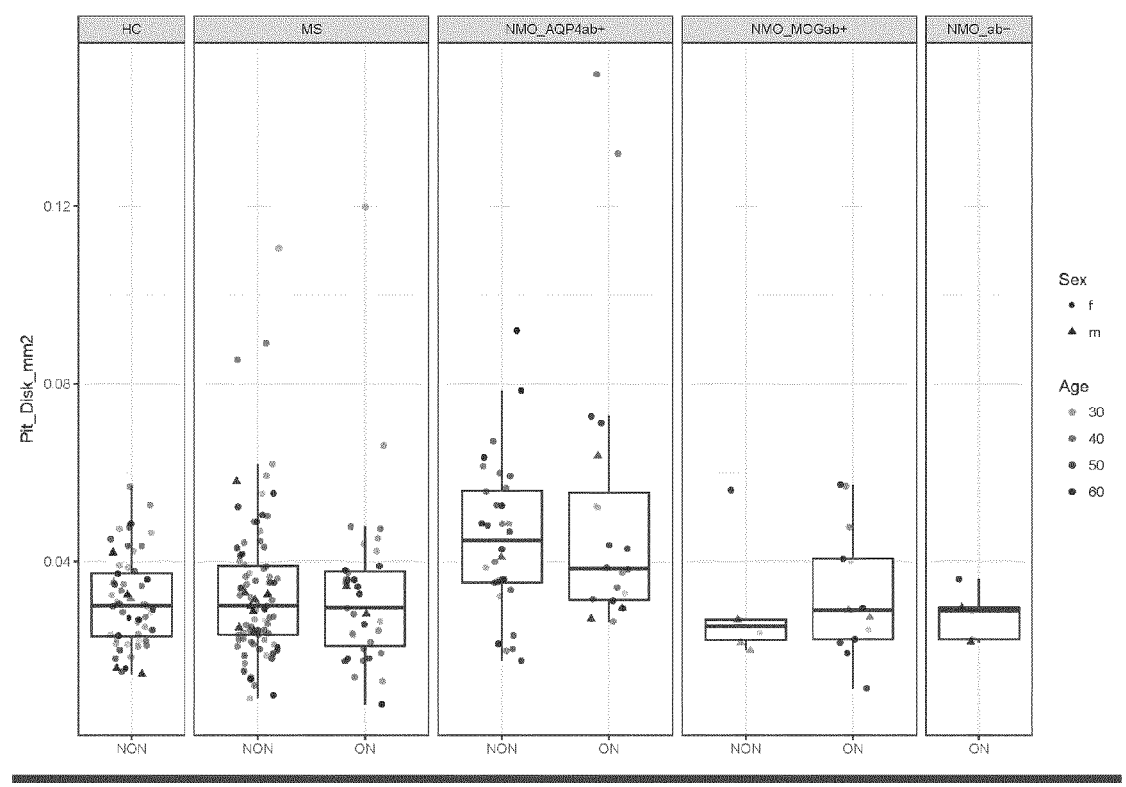

In FIG. 24 the results from the cohort of table 4 for the shape parameter 'pit disk area' $A_f$ ("pit disk") are shown. The pit disk area $A_f$ is measured in $mm^2$.

Figure 25:
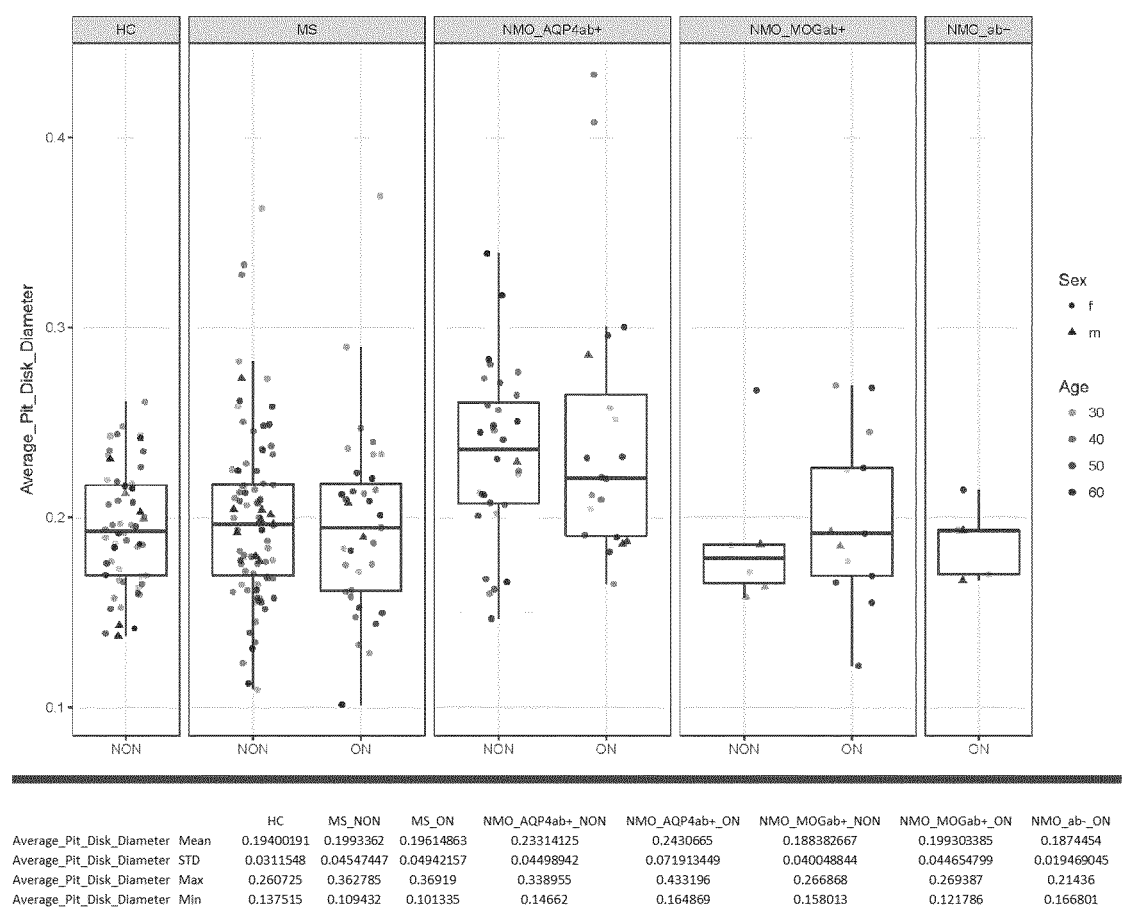

In FIG. 25 the results from the cohort of table 4 for the shape parameter 'average pit disk diameter' $d_f$ are shown. The average pit disk diameter $d_f$ is measured in mm.

Figure 26:
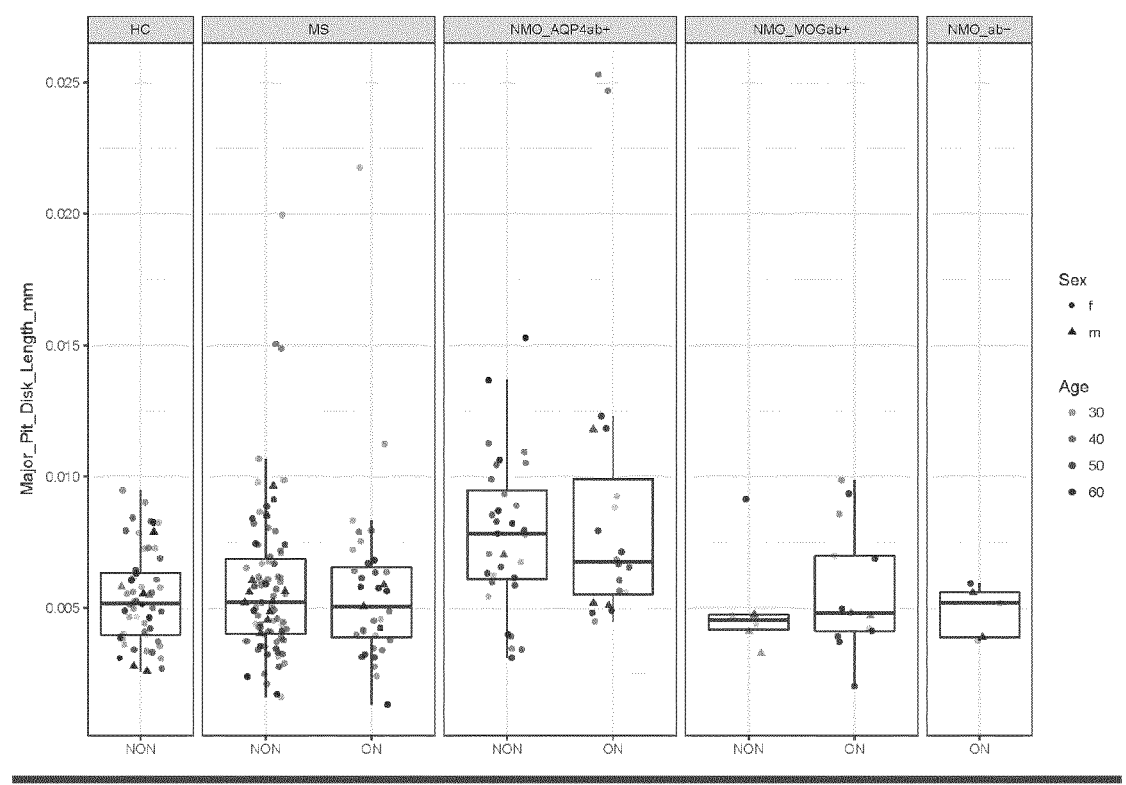

In FIG. 26 the results from the cohort of table 4 for the shape parameter 'major axis length of the pit disk area' $\lambda_3^f$ ("major pit disk length") are shown. The major axis length $\lambda_3^f$ is measured in mm.

Figure 27:
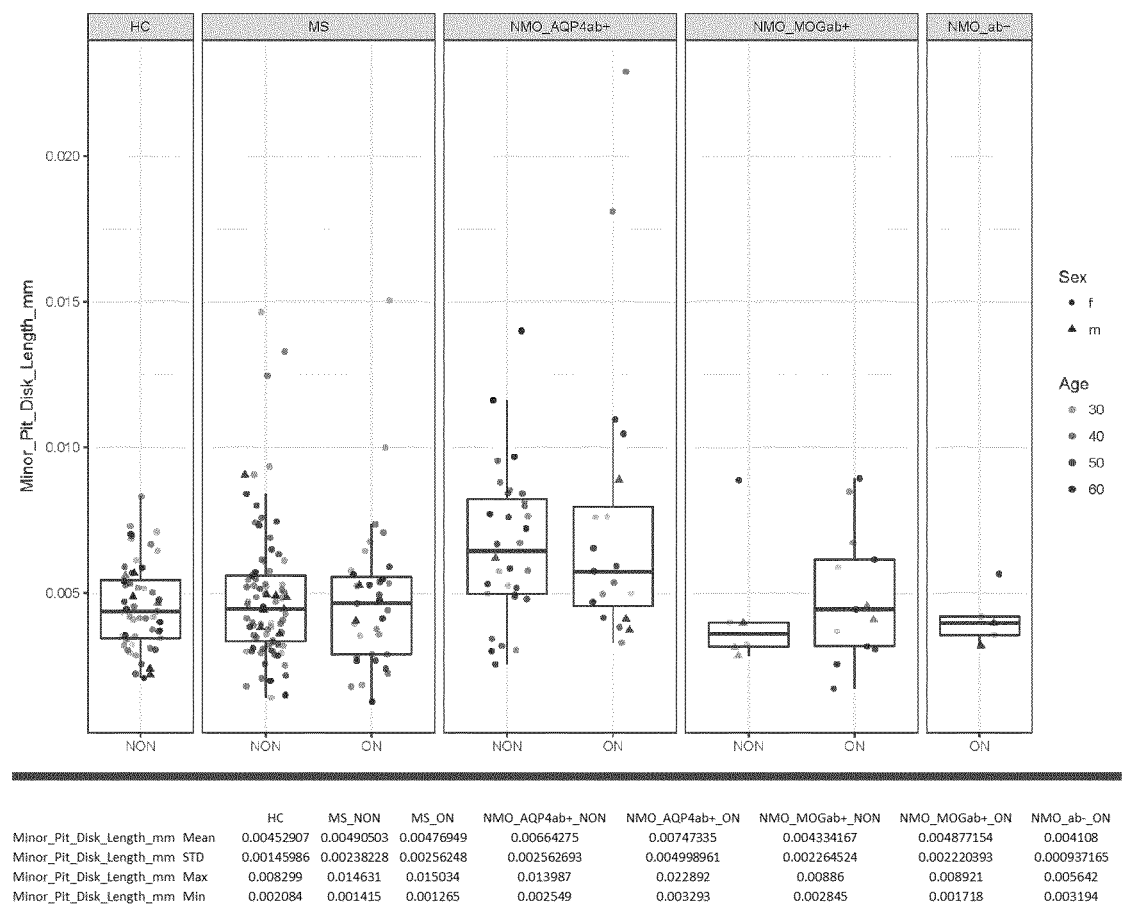

In FIG. 27 the results from the cohort of table 4 for the shape parameter 'minor axis length of the pit disk area' $\lambda_2^f$ ("minor pit disk length") are shown. The minor axis length $\lambda_2^f$ is measured in mm.

Figure 28:
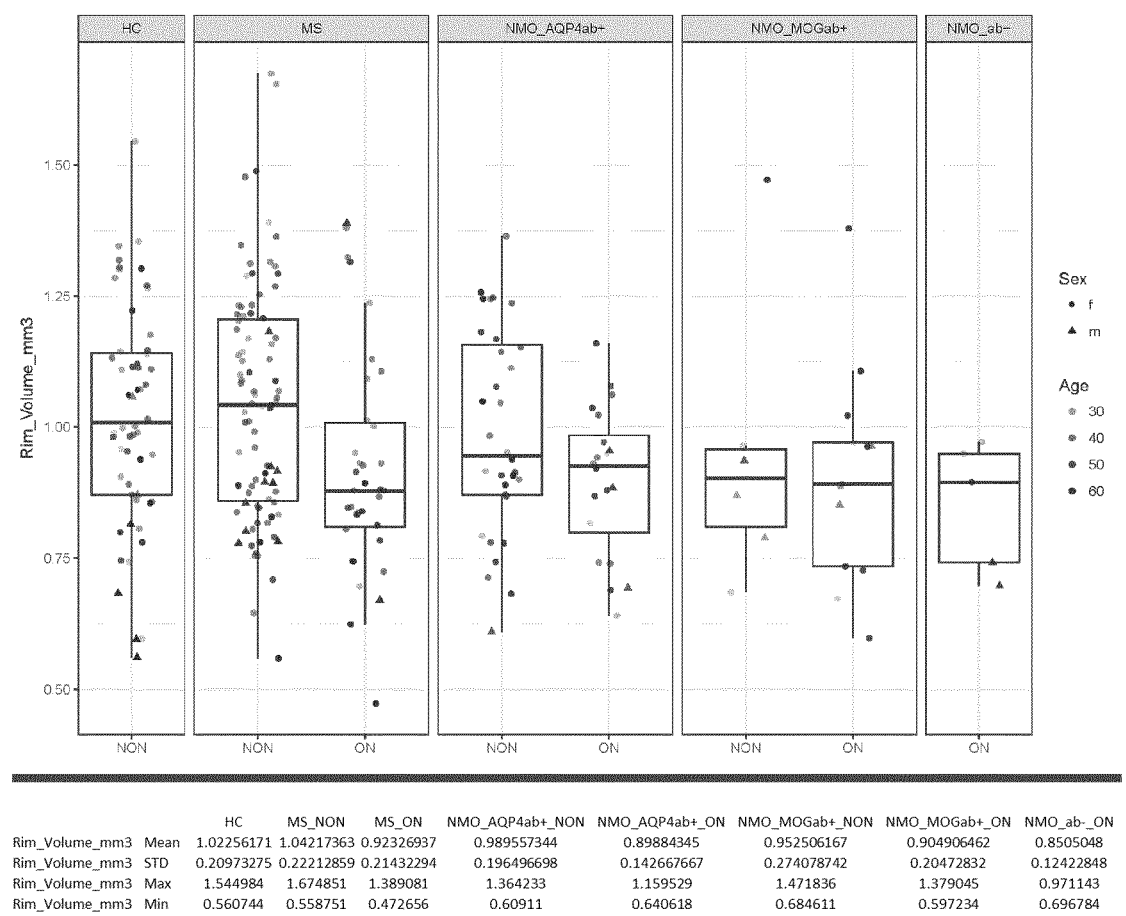

In FIG. 28 the results from the cohort of table 4 for the shape parameter 'rim volume' $V_r$ are shown. The rim volume $V_r$ is measured in $mm^3$.

Figure 29:
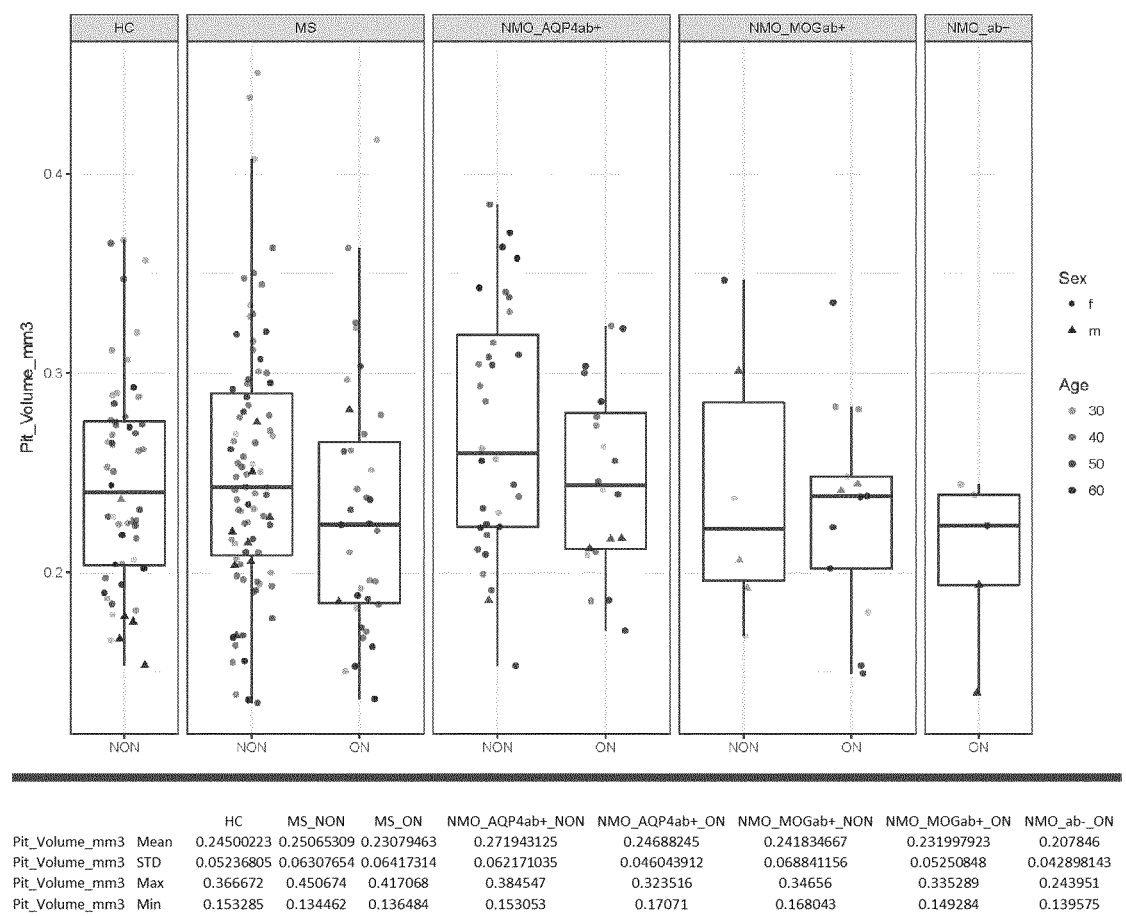

In FIG. 29 the results from the cohort of table 4 for the shape parameter 'pit volume' $V_p$ are shown. The pit volume $V_p$ is measured in $mm^3$.

Figure 30:
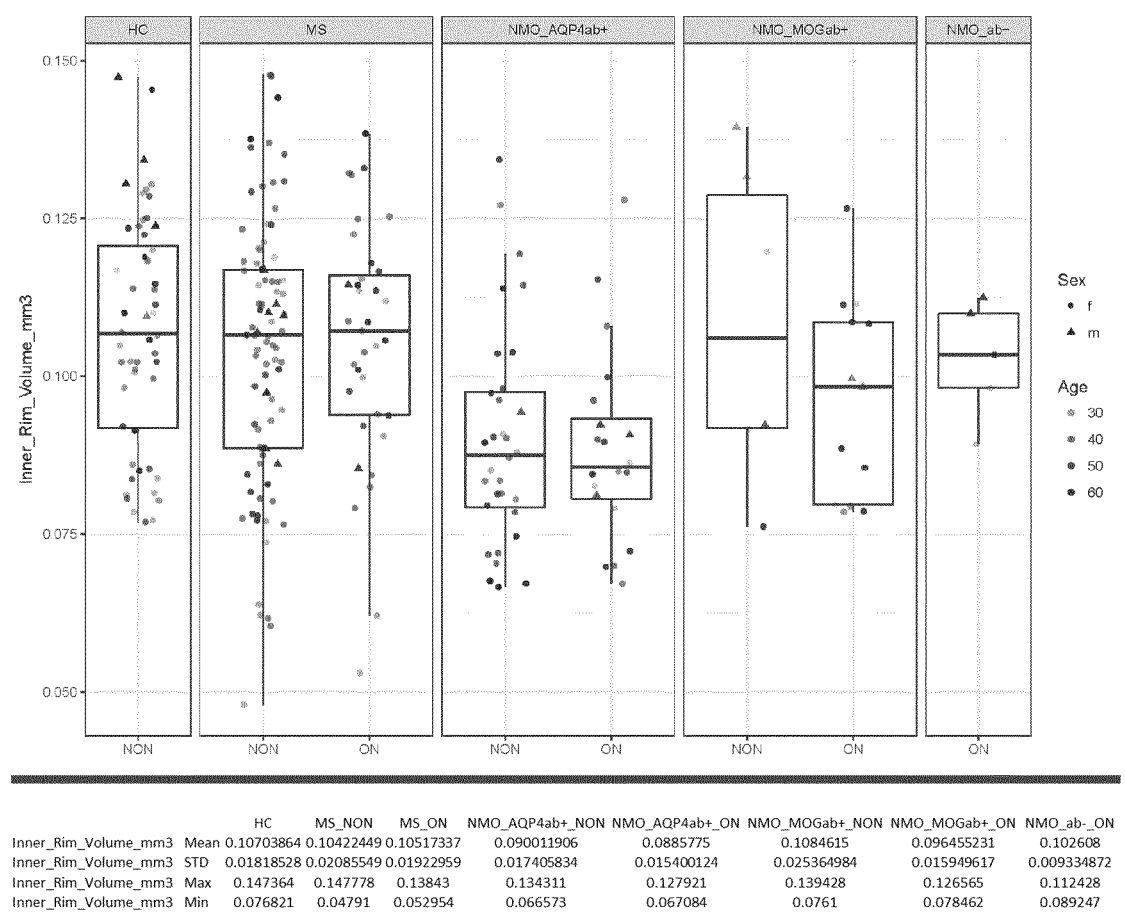

In FIG. 30 the results from the cohort of table 4 for the shape parameter 'inner rim volume' $V_{IR}$ are shown. The rim volume $V_{IR}$ is measured in $mm^3$.

Figure 31:
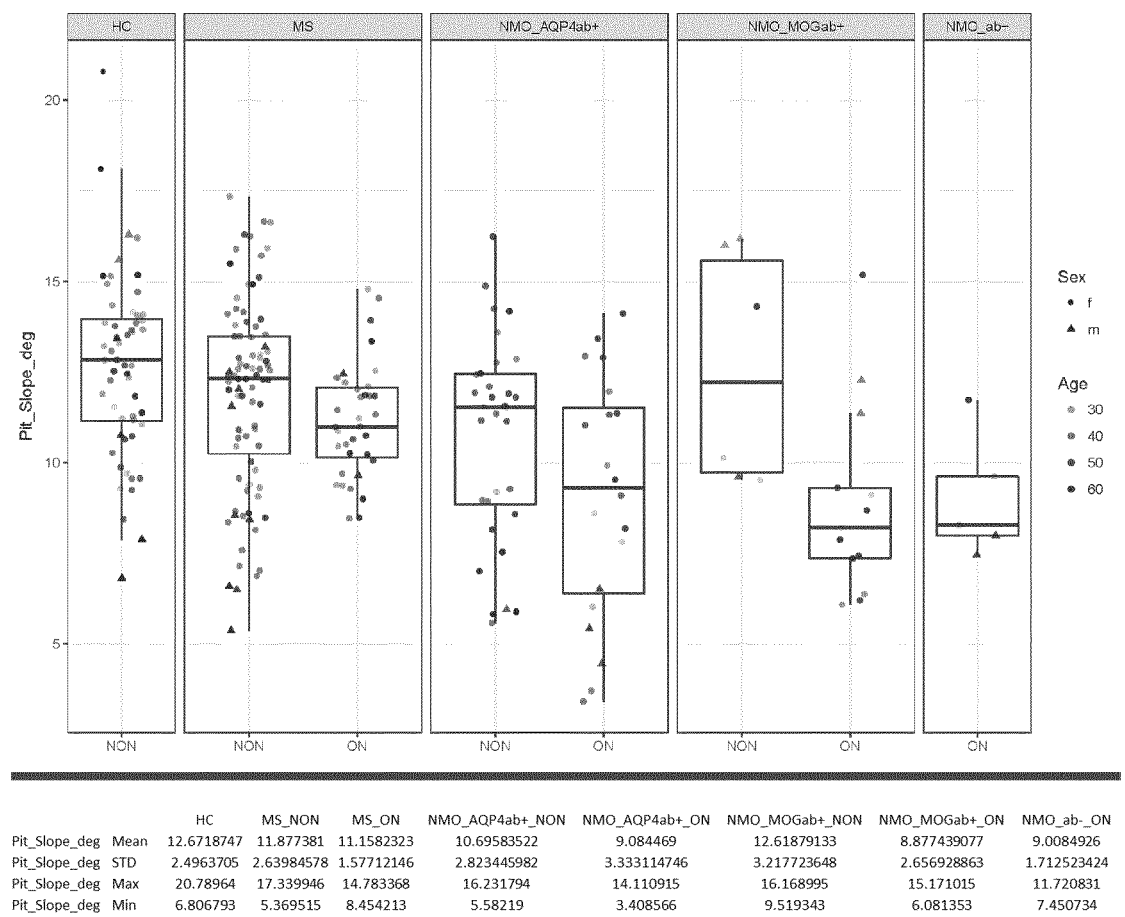

In FIG. 31 the results from the cohort of table 4 for the shape parameter 'average maximum pit slope' $s_m$ ("pit slope") are shown. The average maximum pit slope $s_m$ is measured in degrees (deg).

FIG. 32 depicts Table 5, a performance of the classification of patients of the MS and HS group.

FIG. 33 depicts Table 6, a performance of the classification of patients of the HS group only.

FIG. 34 depicts Table 6, a performance of the classification of patients of the MS group only.

The performance of the classification of patients according to the invention with respect to a differential diagnosis of NMO-patients tested positive with Aquaporin-4 antibody test with respect to the HC and MS group, with respect to the HC only or with respect to MS-patients only, by using all shape parameters and conventional parameters, is given in Table 5, Table 6 and Table 7, respectively.

In Tables 5-7 (cf. FIGS. 32 to 34), the numbers in the bold framed squares indicate the correct assignment of the health condition by the method according to the invention. The numbers in the thin framed squares indicate a false classification of the health condition. Thus, the top left square represents true positive, the bottom right square represents the true negative, bottom left square represents false positive (Type I error) and the top right square represents false negative (Type II error).

Table 5 (FIG. 32) depicts a performance of the classification of patients according to the invention with respect to a differential diagnosis of NMO-patients tested positive with Aquaporin-4 antibody test with respect to the HC and MS group, by using all shape parameters and conventional parameters.

Table 6 (FIG. 33) depicts a performance of the classification of patients according to the invention with respect to a differential diagnosis of NMO-patients tested positive with Aquaporin-4 antibody test with respect to the HC only, by using all shape parameters and conventional parameters.

Table 7 (FIG. 34) depicts a performance of the classification of patients according to the invention with respect to a differential diagnosis of NMO-patients tested positive with Aquaporin-4 antibody test with respect to MS-patients only, by using all shape parameters and conventional parameters.

7. CONCLUSION

The method according to the invention provides a reliable, accurate and meaningful approach for fovea shape analysis, which is able to correctly model the profile of the foveal region and reconstruct its 3D shape. The method according to the invention has been shown to robustly encounter possible variations in foveal shape in HC but also in foveae that undergo considerable changes during the course of a neuroinflammatory disease. The mathematical model created is simple and has the advantage of a straight forward derivation of parameters. The computed parameters are in direct relation to the geometry modeled, and therefore provide an intuitive way of interpretation for further medical analysis and clinical interpretation. A major advancement of the developed method is that it is possible to analyze the foveal shape in a clinical context, especially from the 3D perspective. Several derived foveal shape parameters show statistically, significant differences between HC and patients with neuroinflammatory diseases of the central nervous system.

REFERENCES AND LINKS

[1] Ding, Y., Spund, B., Glazman, S., Shrier, E. M., Miri, S., Selesnick, I., and Bodis-Wollner, I. Application of an oct data-based mathematical model of the foveal pit in parkinson disease. *Journal of Neural Transmission* 121, 11 (2014), 1367-1376.
[2] Dubis, A. M., McAllister, J. T., and Carroll, J. Reconstructing foveal pit morphology from optical coherence tomography imaging. *British Journal of Ophthalmology* 93, 9 (2009), 1223-1227.
[3] Farin, G. E. *Curves and Surfaces for Computer-Aided Geometric Design: A Practical Code*, 4th ed. Academic Press, Inc., Orlando, Fla., USA, 1996.
[4] Ihaka, R., and Gentleman, R. R: A language for data analysis and graphics. *Journal of Computational and Graphical Statistics* 5, 3 (1996), 299-314.
[5] Liu, L., Marsh-Tootle, W., Harb, E. N., Hou, W., Zhang, Q., Anderson, H. A., Norton, T. T., Weise, K. K., Gwiazda, J. E., Hyman, L., and the COMET Group. A sloped piecemeal Gaussian model for characterizing foveal pit shape. *Ophthalmic and Physiological Optics* 36, 6 (November 2016), 615-631.
[6] Oberwahrenbrock, T., Ringelstein, M., Jentschke, S., Deuschle, K., Klumbies, K., Bellmann-Strobl, J., Harmel, J., Ruprecht, K., Schippling, S., Hartung, H. P., Aktas, O., Brandt, A. U., and Paul, F. Retinal ganglion cell and inner plexiform layer thinning in clinically isolated syndrome. *Multiple Sclerosis Journal* 19, 14 (2013), 1887-1895.
[7] Oertel, F. C., Kuchling, J., Zimmermann, H., Chien, C., Schmidt, F., Knier, B., Bellmann-Strobl, J., Korn, T., Scheel, M., Klistorner, A., Ruprecht, K., Paul, F., and Brandt, A. U. Microstructural visual system changes in AQP4-antibody-seropositive NMOSD. *Neurology—Neuroimmunology Neuroinflammation* 4, 3 (February 2017), e334.
[8] Oertel, F. C., Zimmermann, H., Mikolajczak, J., Weinhold, M., Kadas, E. M., Oberwahrenbrock, T., Pache, F., Bellmann-Strobl, J., Ruprecht, K., Paul, F., and Brandt, A. U. Contribution of blood vessels to retinal nerve fiber layer thickness in nmosd. *Neurology—Neuroimmunology Neuroinflammation* 4, 3 (2017).
[9] Scheibe, P., Lazareva, A., Braumann, U. D., Reichenbach, A., Wiedemann, P., Francke, M., and Rauscher, F. G. Parametric model for the 3d reconstruction of individual fovea shape from OCT data. *Experimental Eye Research* 119 (February 2014), 19-26.
[10] Scheibe, P., Zocher, M. T., Francke, M., and Rauscher, F. G. Analysis of foveal characteristics and their asymmetries in the normal population. *Experimental Eye Research* 148 (July 2016), 1-11.
[11] Schneider, E., Zimmermann, H., Oberwahrenbrock, T., Kaufhold, F., Kadas, E. M., Petzold, A., Bilger, F., Borisow, N., Jarius, S., Wildemann, B., Ruprecht, K., Brandt, A. U., and Paul, F. Optical coherence tomography reveals distinct patterns of retinal damage in neuromyelitis optica and multiple sclerosis. *PLOS ONE* 8, 6 (June 2013), 1-10.

The invention claimed is:

1. A method for estimating shape parameters of an image data set (1) of a fovea (100), comprising the steps of:
Acquiring an image data set (1) of the macula (50) of an eye, the macula comprising a foveal pit (101) and a foveal rim (102),
Estimating the center of the foveal pit (101) from the image data set (1),
Estimating from the center of the foveal pit (101), radially extending height profiles (c) of the fovea (100),
For each height profile (c), fitting a model-function to the height profile (c),
Estimating for each height profile (c) a set of fit parameters from the fitted model-function, and
Determining from the sets of fit parameters at least one shape parameter of the fovea (100),
wherein the model function is a smooth composite Bézier path comprising cubic Bézier functions, and
wherein each height profile (c) comprises an interior segment ($c_I$) and an exterior segment ($c_E$), wherein the height profiles (c) are fitted with the smooth composite Bézier path, wherein a first Bézier function ($Q_I$) is fitted to the interior segment ($c_I$) and wherein a second Bézier function ($Q_E$) is fitted to the exterior segment ($c_E$), wherein the interior segment ($c_I$) extends between a first end point ($P_0^I$) and a second end point ($P_3^I$) of the first Bézier function ($Q_I$), and the exterior segment ($c_E$) extends between a first end point ($P_0^E$) and a second end point ($P_3^E$) of the second Bézier function ($Q_E$), wherein the second end point ($P_3^I$) of the first Bézier function ($Q_I$) is identical or adjoining with the first end point ($P_0^E$) of the second Bézier function ($Q_E$), wherein the first end point ($P_0^I$) of the first Bézier function ($Q_I$) is at a first end of the height profile (c), the second end point ($P_3^I$) of the first Bézier function ($Q_I$) and the first end point ($P_0^E$) of the second Bézier function ($Q_E$) are identical at a maximum rim height of the height profile (c) and the second end point ($P_3^E$) of the second Bézier function ($B_2$) is at a second end of the height profile (c), wherein the first and second Bézier function ($Q_I$, $Q_E$) have the same slope at the second end point ($P_3^I$) of the first Bézier function ($Q_I$) and the identical first end point ($P_0^E$) of the second Bézier function ($Q_E$).

2. Method according to claim 1, wherein the height profiles (c) each comprise segments, wherein each segment is fitted with the Bézier function comprised by the smooth composite Bézier path.

3. Method according to claim 1, wherein each height profile (c) is determined from a surface data set (200), wherein the surface data set (200) comprises a distance between the inner limiting membrane (103) representing data and the retinal pigment epithelium layer (104) representing data comprised in the image data set (100), wherein the height profiles (c) are line profiles along the respective radial direction of the surface data set (200).

4. Method according to claim 1, wherein the height profiles (c) are regularly spaced.

5. Method according to claim 1, wherein the at least one determined shape parameter of the fovea (100) is one of the following:
A central foveal thickness ($h_{cft}$),
An average rim height ($h_r$)
A rim disk area ($A_r$),
A minor axis and a minor axis length ($\lambda_2^r$) of the rim disk area ($A_r$),
A major axis and a major axis length ($\lambda_3^r$) of the rim disk area ($A_r$),
An average rim disk diameter ($d_r$),
An average pit depth ($h_p$),
An average maximum pit slope ($s_m$),
An average slope disk diameter ($d_s$),
A slope disk area ($A_s$),
A minor axis and a minor axis length ($\lambda_2^s$) of the slope disk area ($A_s$),
A major axis and a major axis length ($\lambda_3^s$) of the slope disk area ($A_s$),
A pit disk area ($A_f$),
A minor axis and a minor axis length ($\lambda_2^f$) of the pit disk area ($A_f$),
A major axis and a major axis length ($\lambda_3^f$) of the pit disk area ($A_f$), An average pit disk diameter ($d_f$)

A rim volume ($V_r$),

An inner rim volume ($V_{IR}$), and/or

A pit volume ($V_p$).

6. Method according to claim 5, wherein a first set of shape parameters associated to a first morphological group of the fovea (100) comprises:

The minor axis length ($\lambda_2^s$) of the slope disk area ($A_s$),

The slope disk area ($A_s$), and

The average slope disk diameter ($d_s$).

7. Method according to claim 5, wherein a second set of shape parameters associated to a second morphological group of the fovea (100) comprises:

The average rim height ($h_r$),

The major axis length ($\lambda_3^s$) of the slope disk area ($A_s$),

The pit disk area ($A_f$),

The average pit disk diameter ($d_f$),

The minor axis length ($\lambda_2^f$) of the pit disk area ($A_f$),

The inner rim volume ($V_{IR}$).

8. Method according to claim 5, wherein a third set of shape parameters associated to a third morphological group of the fovea (100) comprises:

The pit depth ($h_p$),

The major axis length ($\lambda_3^f$) of the pit disk area ($A_f$), and

The average maximum pit slope ($s_m$).

9. Method according to claim 5, wherein a fourth set of shape parameters associated to a fourth morphological group of the fovea (100) comprises:

The central foveal thickness ($h_{cft}$),

The average rim diameter ($d_r$),

The rim disk area ($A_r$),

The major axis length ($\lambda_3^r$) of the rim disk area ($A_r$),

The minor axis length ($\lambda_2^r$) of the rim disk area ($A_r$),

The rim volume ($V_r$),

The pit volume ($V_f$), and

The inner rim volume ($V_{IR}$).

10. Method according to claim 5, wherein the image data set (1) is assigned to a morphological group, wherein the image data set (1) is assigned based on the value of at least one of the shape parameters by comparing the magnitude or deviation of the respective shape parameter to a predefined reference value for the shape parameter.

11. Method according to claim 5, wherein a trained classifier assigns the image data set (1) to a morphological group, wherein the image data set (1) is assigned based on the value of at least one of the shape parameters by comparing the magnitude or deviation of the respective shape parameter to a predefined reference value for the shape parameter.

* * * * *